(12) United States Patent
Bonutti

(10) Patent No.: US 9,044,341 B2
(45) Date of Patent: Jun. 2, 2015

(54) JOINT SPACER

(75) Inventor: Peter M. Bonutti, Effingham, IL (US)

(73) Assignee: Bonutti Skeletal Innovations LLC, Plano, TX (US)

(*) Notice: Subject to any disclaimer, the term of this patent is extended or adjusted under 35 U.S.C. 154(b) by 0 days.

(21) Appl. No.: 10/755,996

(22) Filed: Jan. 13, 2004

(65) Prior Publication Data

US 2004/0254582 A1 Dec. 16, 2004

Related U.S. Application Data

(63) Continuation of application No. 10/163,480, filed on Jun. 5, 2002, now Pat. No. 7,780,670, which is a continuation of application No. 09/569,020, filed on May 11, 2000, now Pat. No. 6,423,063, which is a continuation of application No. 09/137,443, filed on Aug. 20, 1998, now Pat. No. 6,099,531.

(51) Int. Cl.
*A61F 2/44* (2006.01)
*A61B 17/56* (2006.01)
(Continued)

(52) U.S. Cl.
CPC .............. *A61F 2/4455* (2013.01); *A61B 17/562* (2013.01); *A61B 17/86* (2013.01); *A61F 2/38* (2013.01); *A61F 2/442* (2013.01); *A61F 2002/30128* (2013.01); *A61F 2002/30187* (2013.01); *A61F 2002/3023* (2013.01); *A61F 2002/30232* (2013.01); *A61F 2002/30518* (2013.01); *A61F 2002/30556* (2013.01);
(Continued)

(58) Field of Classification Search
CPC ................................ A61F 2/44; A61F 2/4455

USPC .................. 606/61, 60, 86; 623/16.11, 17.11, 623/17.16; 292/343
See application file for complete search history.

(56) References Cited

U.S. PATENT DOCUMENTS 673,783 A * 5/1901 Peters ........................... 292/342
3,426,364 A 2/1969 Lumd
(Continued)

FOREIGN PATENT DOCUMENTS

EP 0773004 A1 5/1997
FR 2727003 A1 5/1996
(Continued)

OTHER PUBLICATIONS

Brochure entitled "Arthrex", "Opening Wedge Osteotomy", Copyright 1998, Arthrex Inc.
(Continued)

*Primary Examiner* — Mary Hoffman
(74) *Attorney, Agent, or Firm* — Panitch Schwarze Belisario & Nadel LLP

(57) ABSTRACT

To change a spatial relationship between two or more bones in a patient's body, a wedge member is moved into a joint between the bones. As the wedge member enters the joint, pivotal movement occurs between the bones to change the orientation of the bones relative to each other. The wedge member may have a porous construction which enables bone to grow through the wedge member and immobilize the joint. The wedge member may be coated with and/or contain bone growth promoting material. The wedge member may be connected to only one of the bones or may be connected to two adjacent bones. If the wedge member is connected to only one bone, the joint may be capable of being flexed after the wedge member is inserted into the joint.

47 Claims, 9 Drawing Sheets

(51) Int. Cl.
  *A61B 17/86* (2006.01)
  *A61F 2/38* (2006.01)
  *A61F 2/30* (2006.01)
  *A61B 17/80* (2006.01)

(52) U.S. Cl.
  CPC .............. *A61F2002/30578* (2013.01); *A61F 2002/30622* (2013.01); *A61F 2002/30736* (2013.01); *A61F 2002/30754* (2013.01); *A61F 2002/30787* (2013.01); *A61F 2220/0025* (2013.01); *A61F 2230/0008* (2013.01); *A61F 2230/0034* (2013.01); *A61F 2230/0069* (2013.01); *A61F 2250/0009* (2013.01); *A61F 2310/00976* (2013.01); *A61B 17/8095* (2013.01); *Y10S 606/907* (2013.01); *Y10S 606/909* (2013.01)

(56) References Cited

U.S. PATENT DOCUMENTS

| | | |
|---|---|---|
| 3,918,100 A | 11/1975 | Shaw |
| 4,298,993 A * | 11/1981 | Kovaleva et al. ........... 623/22.36 |
| 4,344,193 A | 8/1982 | Kenny |
| 4,349,921 A | 9/1982 | Kuntz |
| 4,385,404 A | 5/1983 | Sully et al. |
| 4,394,370 A * | 7/1983 | Jefferies ........................... 606/76 |
| 4,421,112 A | 12/1983 | Mains et al. |
| 4,450,591 A | 5/1984 | Rappaport |
| 4,502,161 A | 3/1985 | Wall |
| 4,516,276 A | 5/1985 | Mittelmeier et al. |
| 4,599,086 A | 7/1986 | Doty |
| 4,713,076 A * | 12/1987 | Draenert ........................ 623/23.6 |
| 4,772,287 A | 9/1988 | Ray et al. |
| 4,808,185 A | 2/1989 | Penenberg et al. |
| 4,829,152 A | 5/1989 | Rostoker |
| 4,877,020 A | 10/1989 | Vich |
| 4,880,429 A | 11/1989 | Stone |
| 4,904,261 A * | 2/1990 | Dove et al. ................. 623/17.16 |
| 4,917,704 A | 4/1990 | Frey |
| 4,919,667 A | 4/1990 | Richmond |
| 4,955,908 A | 9/1990 | Frey |
| 4,961,740 A | 10/1990 | Ray et al. |
| 5,006,120 A | 4/1991 | Carter |
| 5,015,255 A | 5/1991 | Kuslich |
| 5,022,576 A * | 6/1991 | Jenq ................................. 225/20 |
| 5,026,373 A | 6/1991 | Ray et al. |
| 5,030,233 A | 7/1991 | Ducheyne |
| 5,041,129 A | 8/1991 | Hayhurst |
| 5,053,039 A | 10/1991 | Hofmann et al. |
| 5,061,286 A * | 10/1991 | Lyle ............................. 623/23.63 |
| 5,108,438 A | 4/1992 | Stone |
| 5,116,374 A | 5/1992 | Stone |
| 5,192,327 A | 3/1993 | Brantigan |
| 5,201,736 A | 4/1993 | Strauss |
| 5,203,787 A | 4/1993 | Noblitt |
| 5,258,031 A | 11/1993 | Salib et al. |
| 5,282,861 A | 2/1994 | Kaplan |
| 5,306,309 A | 4/1994 | Wagner |
| 5,331,975 A | 7/1994 | Bonutti |
| 5,360,450 A | 11/1994 | Giannini |
| 5,390,683 A | 2/1995 | Pisharodi |
| 5,397,364 A | 3/1995 | Kozak et al. |
| 5,405,391 A | 4/1995 | Hednerson |
| 5,425,772 A | 6/1995 | Brantigan |
| 5,443,514 A | 8/1995 | Steffee |
| 5,458,638 A * | 10/1995 | Kuslich et al. ............. 623/17.11 |
| 5,484,437 A | 1/1996 | Michelson |
| 5,514,180 A * | 5/1996 | Heggeness et al. ........ 623/17.16 |
| 5,550,172 A | 8/1996 | Regula et al. |
| 5,571,191 A | 11/1996 | Fitz |
| 5,601,565 A | 2/1997 | Huebner |
| 5,609,635 A | 3/1997 | Michelson |
| 5,620,448 A | 4/1997 | Puddu |
| 5,645,598 A | 7/1997 | Brosnahan, III |
| 5,653,761 A | 8/1997 | Pisharodi |
| 5,653,762 A | 8/1997 | Pisharodi |
| 5,658,336 A | 8/1997 | Pisharodi |
| 5,669,909 A | 9/1997 | Zdeblick et al. |
| 5,683,463 A | 11/1997 | Godefroy et al. |
| 5,683,464 A | 11/1997 | Wagner et al. |
| 5,702,454 A | 12/1997 | Baumgartner |
| 5,713,899 A | 2/1998 | Marnay et al. |
| 5,716,415 A | 2/1998 | Steffee |
| 5,722,978 A | 3/1998 | Jenkins |
| 5,766,251 A | 6/1998 | Koshino |
| 5,766,252 A | 6/1998 | Henry et al. |
| 5,769,897 A | 6/1998 | Harle |
| 5,776,199 A | 7/1998 | Michelson |
| 5,785,710 A | 7/1998 | Michelson |
| 5,807,403 A | 9/1998 | Beyar |
| 5,814,084 A | 9/1998 | Grivas et al. |
| 5,836,948 A | 11/1998 | Zucherman et al. |
| 5,865,845 A | 2/1999 | Thalgott |
| 5,888,223 A | 3/1999 | Bray, Jr. |
| 5,888,224 A | 3/1999 | Beckers |
| 5,888,227 A | 3/1999 | Cottle |
| 5,888,228 A * | 3/1999 | Knothe et al. ............. 623/17.16 |
| 5,895,426 A | 4/1999 | Scarborough et al. |
| 5,904,719 A | 5/1999 | Errico et al. |
| 5,906,616 A | 5/1999 | Pavlov et al. |
| 5,916,267 A * | 6/1999 | Tienboon ................... 623/17.11 |
| 5,984,967 A | 11/1999 | Zdeblick et al. |
| 5,989,289 A | 11/1999 | Coates et al. |
| 6,001,099 A | 12/1999 | Huebner |
| 6,007,580 A | 12/1999 | Lehto |
| 6,008,433 A | 12/1999 | Stone |
| 6,042,582 A | 3/2000 | Ray |
| 6,045,579 A | 4/2000 | Hochshuler et al. |
| 6,066,175 A | 5/2000 | Henderson et al. |
| 6,086,593 A | 7/2000 | Bonutti |
| 6,099,531 A | 8/2000 | Bonutti |
| 6,102,950 A | 8/2000 | Vaccaro |
| 6,136,031 A | 10/2000 | Middleton |
| 6,190,414 B1 | 2/2001 | Young |
| 6,206,922 B1 | 3/2001 | Zdeblick et al. |
| 6,206,927 B1 | 3/2001 | Fell et al. |
| 6,241,771 B1 | 6/2001 | Gresser et al. |
| 6,251,140 B1 | 6/2001 | Marino et al. |
| 6,290,724 B1 | 9/2001 | Marino |
| 6,368,325 B1 | 4/2002 | McKinley |
| 6,423,063 B1 | 7/2002 | Bonutti |
| 6,432,106 B1 | 8/2002 | Fraser |
| 6,458,158 B1 | 10/2002 | Anderson et al. |
| 6,458,159 B1 | 10/2002 | Thalgott |
| 6,471,724 B2 * | 10/2002 | Zdeblick et al. ........... 623/17.16 |
| 6,482,233 B1 | 11/2002 | Aebi et al. |
| 6,575,982 B1 | 6/2003 | Bonutti |
| 6,613,091 B1 | 9/2003 | Zdeblick et al. |
| 6,823,871 B2 | 11/2004 | Schmieding |
| 6,887,248 B2 | 5/2005 | McKinley et al. |
| 6,923,810 B1 | 8/2005 | Michelson |
| 7,001,385 B2 | 2/2006 | Bonutti |
| 7,128,763 B1 | 10/2006 | Blatt |
| 7,776,094 B2 | 8/2010 | McKinley et al. |
| 8,092,537 B2 | 1/2012 | McGahan et al. |
| 8,192,492 B2 | 6/2012 | Robie |
| 8,470,044 B2 | 6/2013 | Bertholet et al. |
| 8,568,484 B2 | 10/2013 | Robie |
| 8,801,785 B2 | 8/2014 | Brittan et al. |
| 2002/0116065 A1 | 8/2002 | Jackson |
| 2002/0156478 A1 | 10/2002 | Bonutti |
| 2003/0028249 A1 | 2/2003 | Baccelli et al. |
| 2003/0199881 A1 | 10/2003 | Bonutti |
| 2004/0148026 A1 | 7/2004 | Bonutti |
| 2004/0153072 A1 | 8/2004 | Bonutti |
| 2008/0046090 A1 | 2/2008 | Paul et al. |
| 2008/0051799 A1 | 2/2008 | Bonutti |

(56) References Cited

U.S. PATENT DOCUMENTS

2008/0058822 A1     3/2008    Bonutti
2010/0312290 A1    12/2010    McKinley et al.

FOREIGN PATENT DOCUMENTS

| SU | 562272 | * | 6/1977 | .................. 606/86 |
|----|--------|---|--------|---------------------------|
| WO | 9508306 A1 | | 3/1995 | |
| WO | WO 9508306 | | 3/1995 | |
| WO | 9614802 A1 | | 5/1996 | |
| WO | 9960837 A2 | | 12/1999 | |
| WO | 9960956 A1 | | 12/1999 | |
| WO | 9960957 A1 | | 12/1999 | |

OTHER PUBLICATIONS

Co-Pending U.S. Appl. No. 10/438,705, NonFinal Office Action mailed Dec. 13, 2005.
Co-pending U.S. Appl. No. 10/438,705, Response filed Apr. 13, 2006.
Co-pending U.S. Appl. No. 10/438,705, Final Office Action mailed May 1, 2006.
Co-pending U.S. Appl. No. 10/438,705, Response filed Jun. 30, 2006.
Co-pending U.S. Appl. No. 10/438,705, Advisory Action mailed Jul. 18, 2006.
Co-pending U.S. Appl. No. 10/438,705, Notice of Appeal filed Jul. 28, 2006.
Co-pending U.S. Appl. No. 10/438,705, Pre-Brief Appeal Notice mailed Aug. 17, 2008.
Co-pending U.S. Appl. No. 10/438,705, Appeal Brief filed Oct. 30, 2006.
Co-pending U.S. Appl. No. 10/438,705,Response filed Jun. 25, 2010.
Co-pending U.S. Appl. No. 10/438,705, Appeal Brief filed Jan. 16, 2007.
Co-pending U.S. Appl. No. 10/438,705, Notice of Non-Comply mailed May 30, 2007.
Co-pending U.S. Appl. No. 10/438,705, Appeal Brief filed Jun. 27, 2007.
Co-pending U.S. Appl. No. 10/438,705, NonFinal Office Action mailed Oct. 9, 2007.
Co-pending U.S. Appl. No. 10/438,705, Response filed Jan. 24, 2008.
Co-pending U.S. Appl. No. 10/438,705, Final Office Action mailed May 14, 2008.
Co-pending U.S. Appl. No. 10/438,705, Request for Continued Exam filed Aug. 14, 2008.
Co-pending U.S. Appl. No. 10/438,705, NonFinal Office Action mailed Sep. 3, 2008.
Co-pending U.S. Appl. No. 10/438,705, Preliminary Amendment filed Sep. 3, 2008.
Co-pending U.S. Appl. No. 10/438,705, Response filed Dec. 3, 2008.
Co-pending U.S. Appl. No. 10/438,705, Final Office Action mailed Mar. 17, 2009.
Co-pending U.S. Appl. No. 10/438,705, Request for Continued Exam filed Aug. 17, 2009.
Co-pending U.S. Appl. No. 10/438,705, NonFinal Office Action mailed Jan. 25, 2010.
Co-pending U.S. Appl. No. 10/438,705, response filed Jun. 25, 2010.
Co-pending U.S. Appl. No. 10/438,705, Final Office Action maile Sep. 15, 2010.
Co-pending U.S. Appl. No. 10/756,001, Restriction Requirement mailed Mar. 17, 2005.
Co-pending U.S. Appl. No. 10/756,001,Response filed Apr. 13, 2005.
Co-pending U.S. Appl. No. 10/756,001, Non Final Rejection mailed Jun. 27, 2005.
Co-pending U.S. Appl. No. 10/756,001, Response filed Sep. 27, 2005.
Co-pending U.S. Appl. No. 10/756,001, Final Rejection mailed Dec. 23, 2005.
Co-pending U.S. Appl. No. 10/756,001, Response filed Feb. 23, 2006.
Co-pending U.S. Appl. No. 10/756,001, Non Final Rejection mailed Sep. 8, 2006.
Co-pending U.S. Appl. No. 10/756,001, Response filed Dec. 6, 2006.
Co-pending U.S. Appl. No. 10/756,001, Non Final Rejection mailed Mar. 8, 2007.
Co-pending U.S. Appl. No. 10/756,001, Response filed Jun. 8, 2007.
Co-pending U.S. Appl. No. 10/756,001 Restriction Requirement mailed Aug. 24, 2007.
Co-pending U.S. Appl. No. 10/756,001, Response filed Nov. 26, 2007.
Co-pending U.S. Appl. No. 10/756,001, Response filed Mar. 7, 2008.
Co-pending U.S. Appl. No. 10/756,001, Final Rejection mailed Jul. 10, 2008.
Co-pending U.S. Appl. No. 10/756,001, Non Final Rejection mailed Dec. 29, 2008.
Co-pending U.S. Appl. No. 10/756,001, Response filed Mar. 30, 2009.
Co-pending U.S. Appl. No. 10/756,001, Final Rejection mailed Jun. 9, 2009.
Co-pending U.S. Appl. No. 10/756,001, Response filed Sep. 9, 2009.
Co-pending U.S. Appl. No. 10/756,001, Non Final Rejection mailed Apr. 28, 2010.
Co-pending U.S. Appl. No. 10/756,001, Response filed Jul. 28, 2010.
Co-pending U.S. Appl. No. 10/163,480, Preliminary Amendment filed Jun. 5, 2002.
Co-pending U.S. Appl. No. 10/163,480, Restriction Requirement mailed Mar. 18, 2005.
Co-pending U.S. Appl. No. 10/163,480, Response filed Apr. 13, 2005.
Co-pending U.S. Appl. No. 10/163,480, NonFinal Rejection mailed Jun. 10, 2005.
Co-pending U.S. Appl. No. 10/163,480, Response filed Sep. 27, 2005.
Co-pending U.S. Appl. No. 10/163,480, Final Rejection mailed Jan. 11, 2006.
Co-pending U.S. Appl. No. 10/163,480, Response filed Mar. 13, 2006.
Co-pending U.S. Appl. No. 10/163,480, Advisory Action mailed Apr. 13, 2006.
Co-pending U.S. Appl. No. 10/163,480, Notice of Appeal filed May 11, 2006.
Co-pending U.S. Appl. No. 10/163,480, Appeal Brief filed Jul. 11, 2006.
Co-pending U.S. Appl. No. 10/163,480, Notice Non-Comply mailed Aug. 15, 2006.
Co-pending U.S. Appl. No. 10/163,480, Appeal Brief filed Aug. 15, 2006.
Co-pending U.S. Appl. No. 10/163,480, Examiner's Answer mailed Sep. 19, 2006.
Co-pending U.S. Appl. No. 10/163,480, Reply Brief filedNov. 11, 2006.
Co-pending U.S. Appl. No. 10/163,480, Reply Brief noted mailed Aug. 20, 2007.
Co-pending U.S. Appl. No. 10/163,480, Order Undocketed Appeal Return mailed Dec. 4, 2007.
Co-pending U.S. Appl. No. 10/163,480, Appeal Brief filed Jan. 21, 2008.
Co-pending U.S. Appl. No. 10/163,480, Notice Reply Brief mailed Oct. 30, 2008.
Co-pending U.S. Appl. No. 10/163,480, Decision Examiner Reversed mailed Aug. 21, 2009.
Co-pending U.S. Appl. No. 10/163,480, Miscellaneous Action Hearing Transcript mailed Sep. 11, 2009.
Co-pending U.S. Appl. No. 10/163,480, Notice of Allowance mailed Apr. 2, 2010.
Co-pending U.S. Appl. No. 11/928,262, Restriction Requirement mailed Feb. 5, 2009.
Co-pending U.S. Appl. No. 11/928,262, Response filed Mar. 5, 2009.
Co-pending U.S. Appl. No. 11/928,262, NonFinal Office Action mailed Apr. 2, 2009.
Co-pending U.S. Appl. No. 11/928,262, Response filed Jul. 2, 2009.
Co-pending U.S. Appl. No. 11/928,262, Final Office Action mailed Feb. 4, 2010.

(56) References Cited

OTHER PUBLICATIONS

Co-pending U.S. Appl. No. 11/928,262, Request for Continued Examination filed Aug. 4, 2010.
Co-pending U.S. Appl. No. 11/928,400, Response filed May 25, 2010.
Co-pending U.S. Appl. No. 11/928,400, Restriction Requirement mailed Jul. 13, 2010.
Co-pending U.S. Appl. No. 11/928,400, non-final Office Action mailed Oct. 27, 2010.
Co-pending U.S. Appl. No. 11/928,400, Restriction Requirement mailed Mar. 25, 2010.
Co-pending U.S. Appl. No. 11/928,400, Response filed Aug. 13, 2010.
Office Action issued Apr. 1, 2013 in U.S. Appl. No. 13/745,263.
Office Action issued Oct. 2, 2013 in U.S. Appl. No. 13/745,263.
Office Action issued Jan. 22, 2014 in U.S. Appl. No. 13/847,325 by Bonutti.
Office Action issued Mar. 12, 2014 in U.S. Appl. No. 13/745,263 by Bonutti.
Office Action issued Dec. 19, 2012 in U.S. Appl. No. 11/928,400.
Office Action issued Jun. 21, 2012 in U.S. Appl. No. 10/438,705.
Office Action issued May 13, 2011 in U.S. Appl. No. 11/928,400.
Office Action issued Jun. 27, 2005 in U.S. Appl. No. 10/756,001.
Barrett et al, "T-Fix Endoscopic Meniscal Repair: Technique and Approach to Different Types of Tears," Arthroscopy: The Journal of Arthroscopic and Related Surgery, vol. 11, No. 2, pp. 245-251 (Apr. 1995).
Cobb et al, "Late Correction of Malunited Intercondylar Humeral Fractures," The Journal of Bone and Joint Surgery, vol. 76-B, pp. 622-626 (1994).
Fellinger et al, "Radial Avulsion of the Triangular Fibrocartilage Complex in Acute Wrist Trauma: A New Technique for Arthroscopic Repair," Arthroscopy: The Journal of Arthroscopic and Related Surgery, vol. 13, No. 3, pp. 370-374 (Jun. 1997).
Hecker et al, "Pull-out strength of suture anchors for rotator cuff and Bankart lesion repairs," The American Journal of Sports Medicine, vol. 21, No. 6, pp. 874-879 (Nov.-Dec. 1993).
Hernigou et al, "Proximal Tibial Osteotomy for Osteoarthritis with Varus Deformity: A Ten to Thirteen-Year Follow-up Study," The Journal of Bone and Joint Surgery, vol. 69-A, No. 3, pp. 332-354 (Mar. 1987).
Ibarra et al, "Glenoid Replacement in Total Shoulder Arthroplastly," The Orthopedic Clinics of North America—Total Shoulder Arthroplasty, vol. 29, No. 3, pp. 403-413 (Jul. 1998).
Mosca et al, "Calcaneal Lengthening for Valgus Deformity of the Hindfoot," The Journal of Bone and Joint Surgery, vol. 77-A, No. 4, pp. 500-512 (Apr. 1995).
Murphy et al, "Radial Opening Wedge Osteotomy in Madelung's Deformity," The Journal of Hand Surgery, vol. 21A, No. 6, pp. 1035-1044 (Nov. 1996).
Unilab Surgibone—Orthopaedic Surgery, The Journal of Bone and Joint Surgery, vol. 76-B, No. 2, p. 345 (Mar. 1994).
Office Action issued Aug. 18, 2014 in U.S. Appl. No. 11/928,262.
U.S. Appl. No. 14/445,784 by Bonutti, filed Jul. 29, 2014.
Office Action issued Oct. 2, 2014 in U.S. Appl. No. 14/445,784 by Bonutti.

* cited by examiner

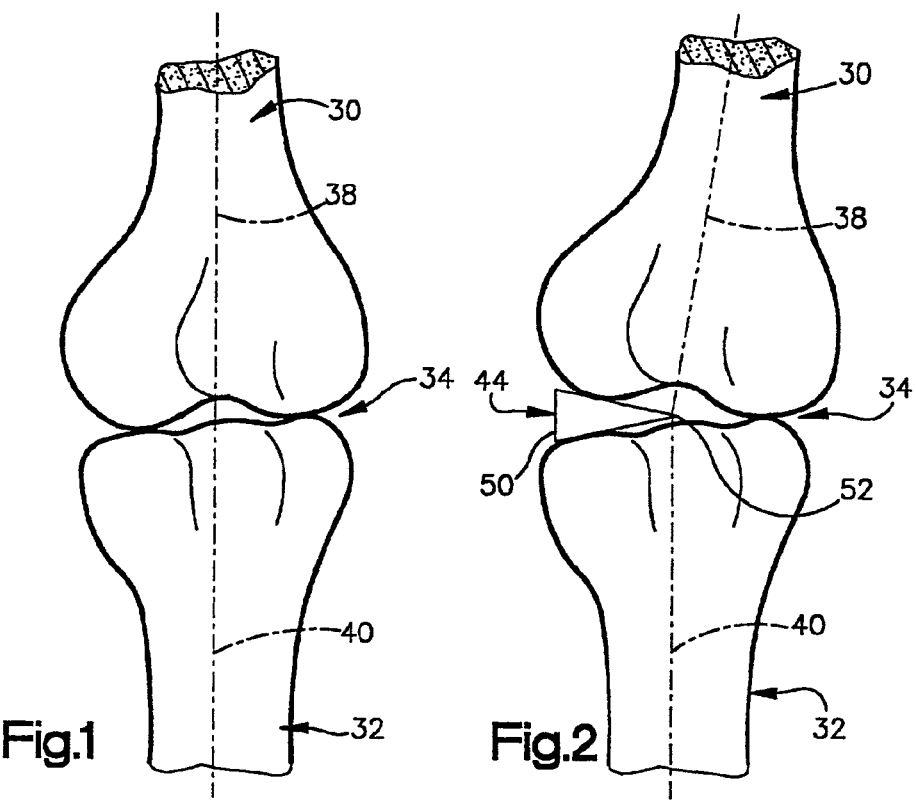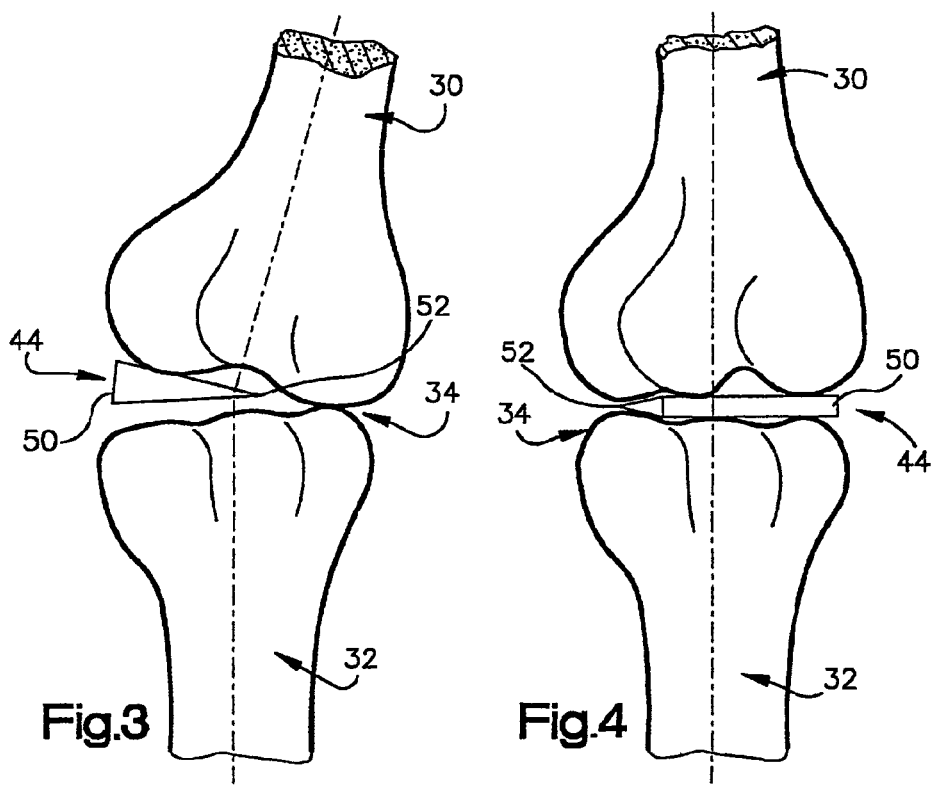

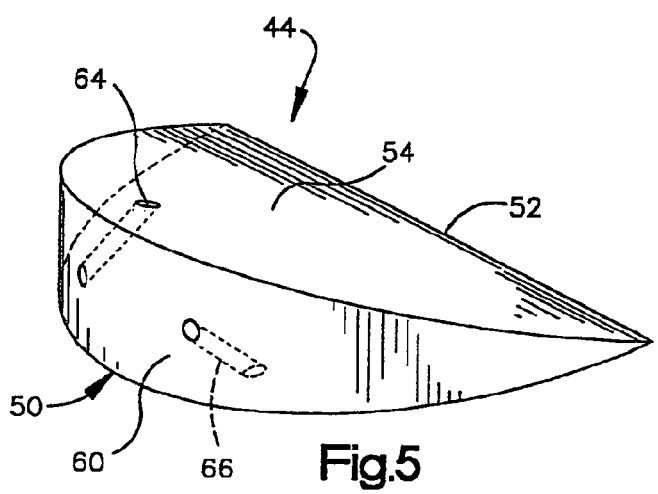
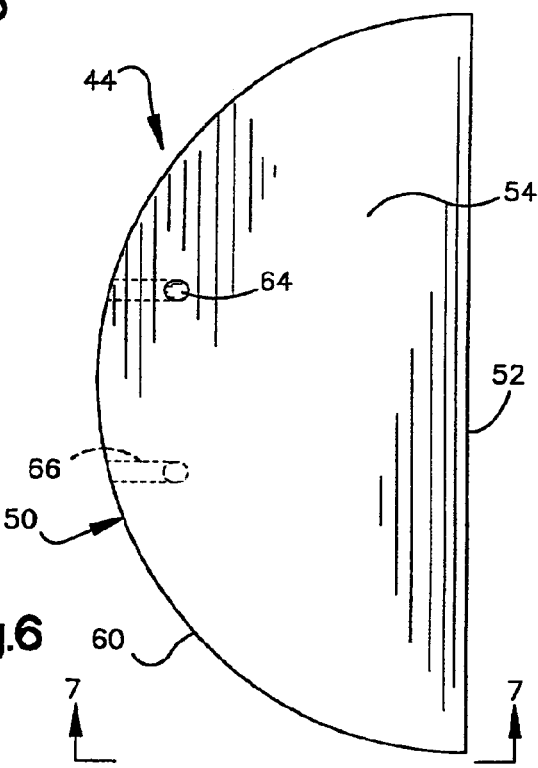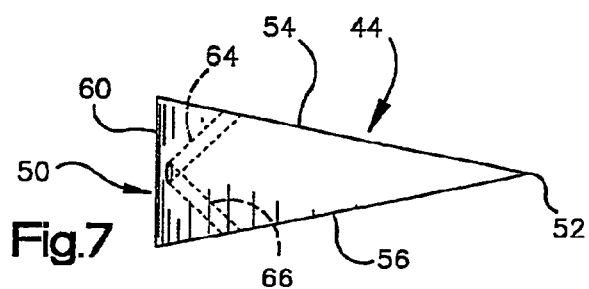

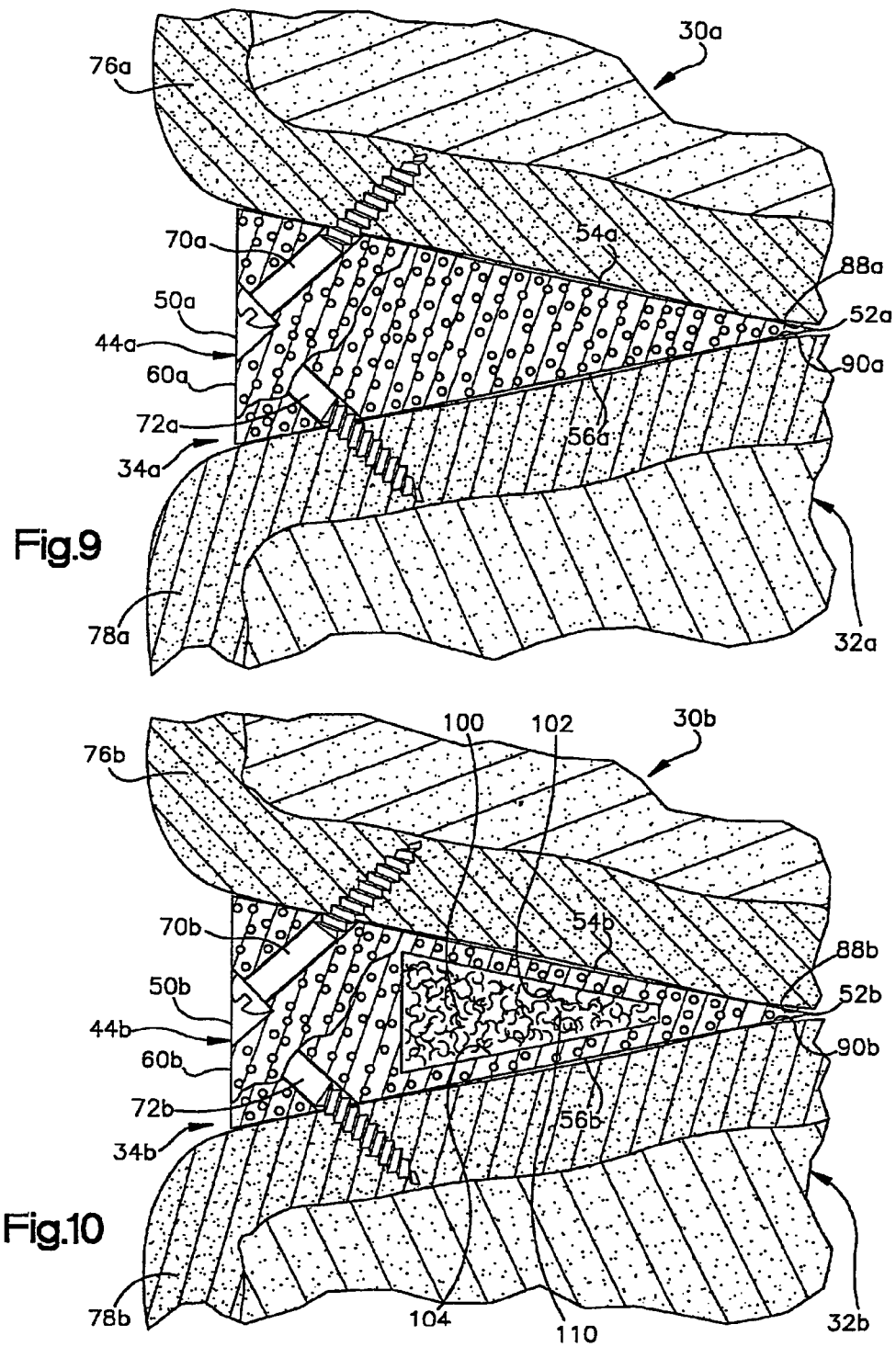

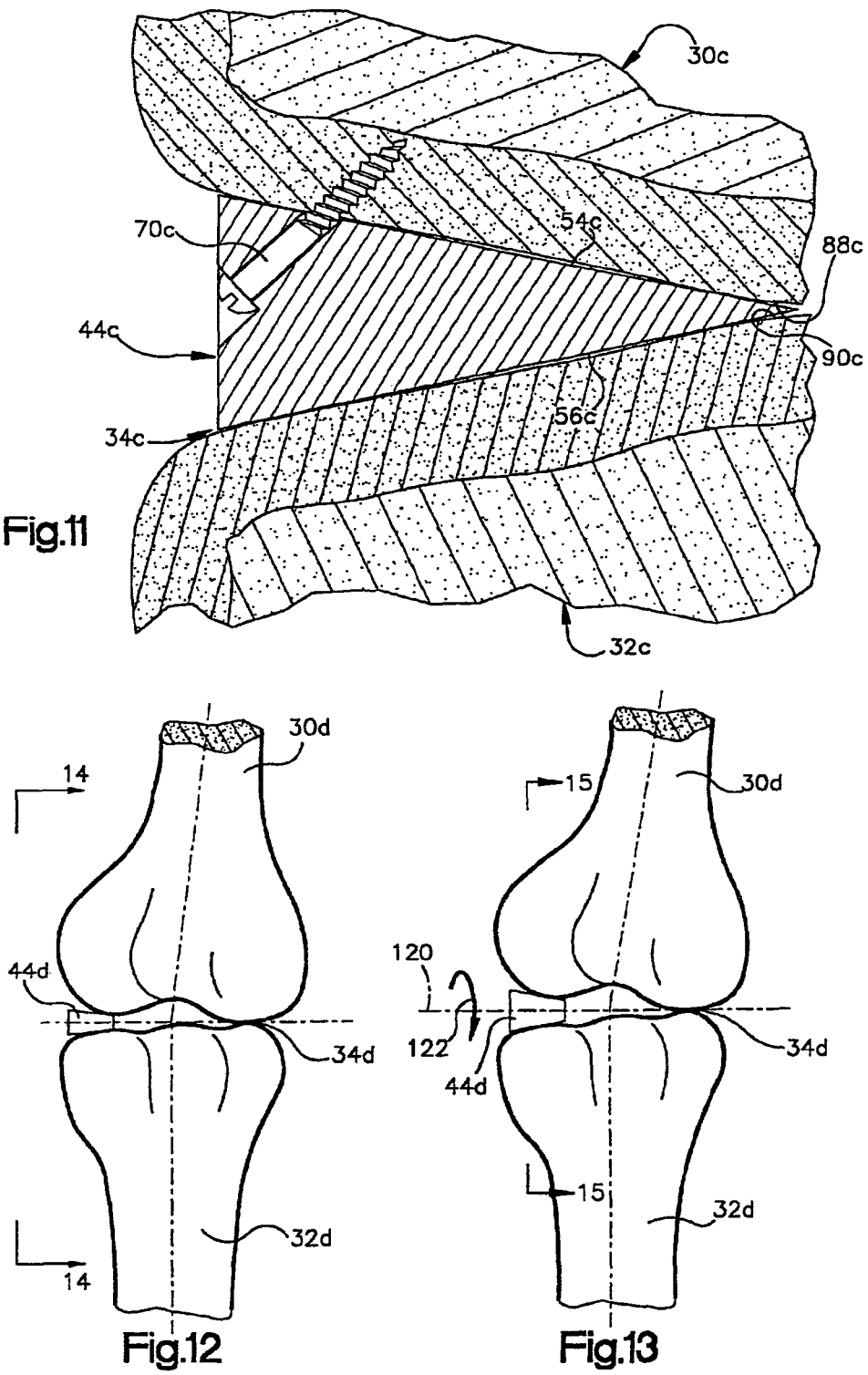

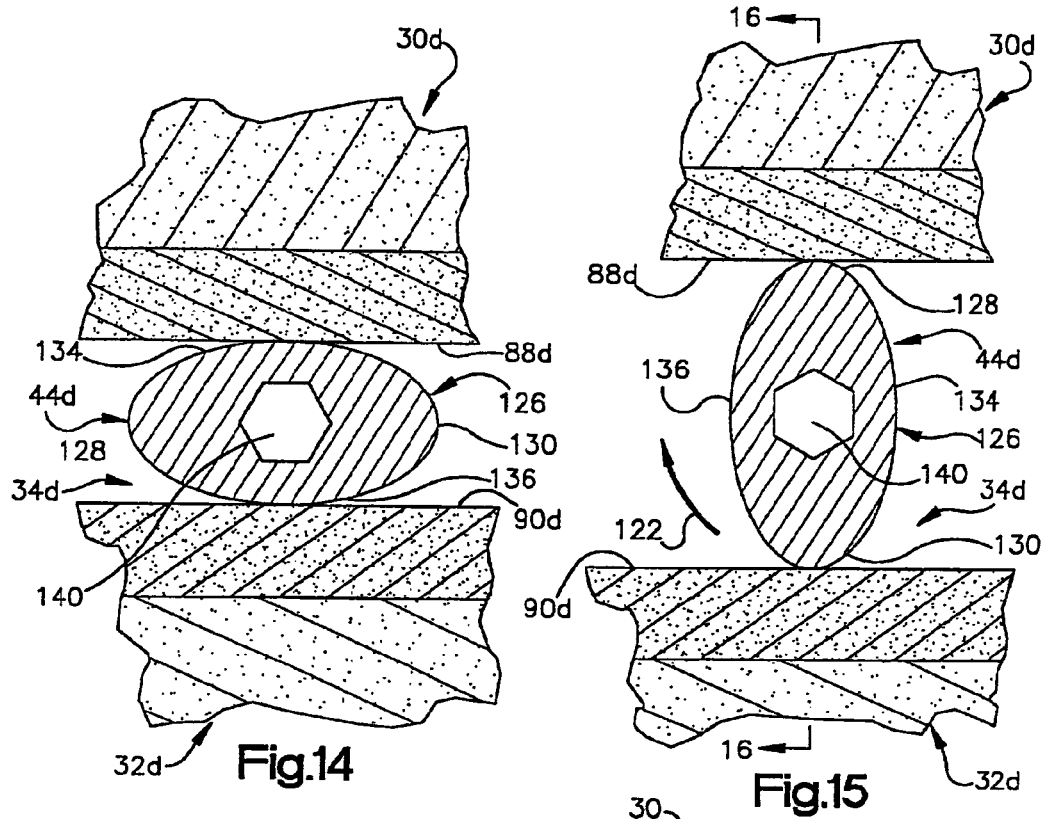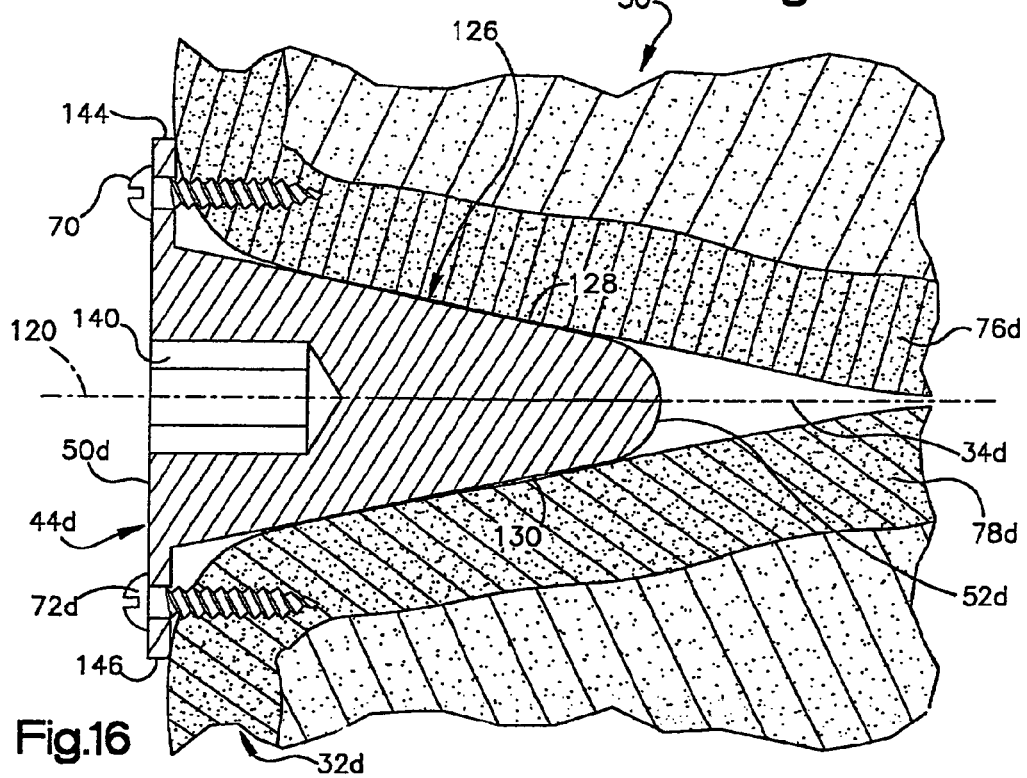

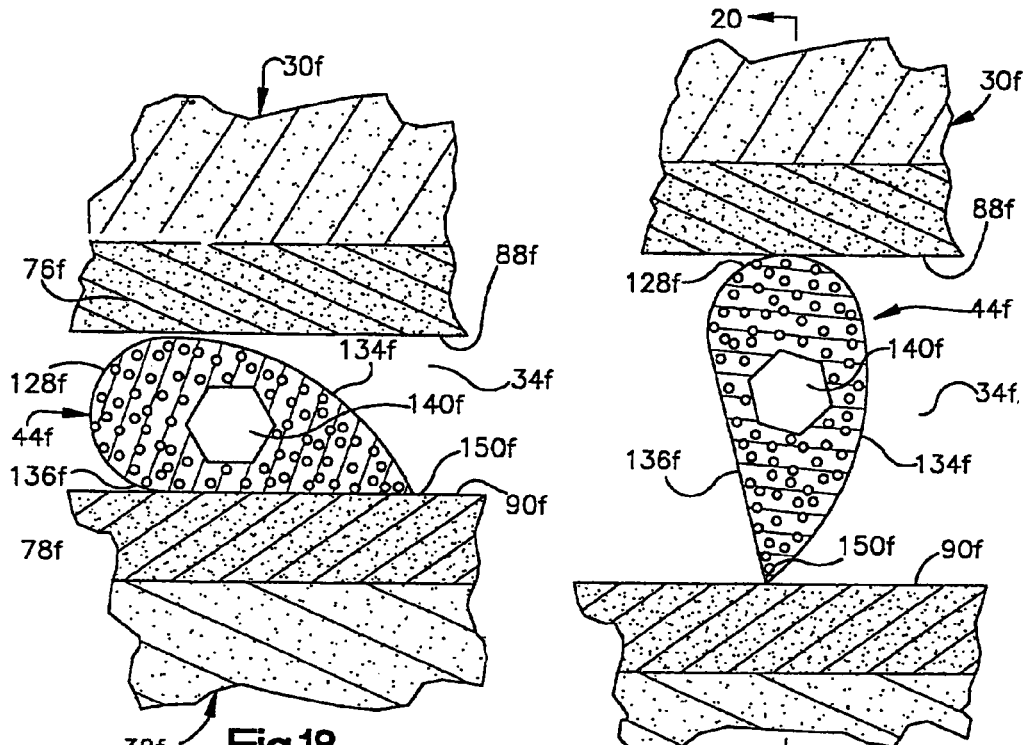
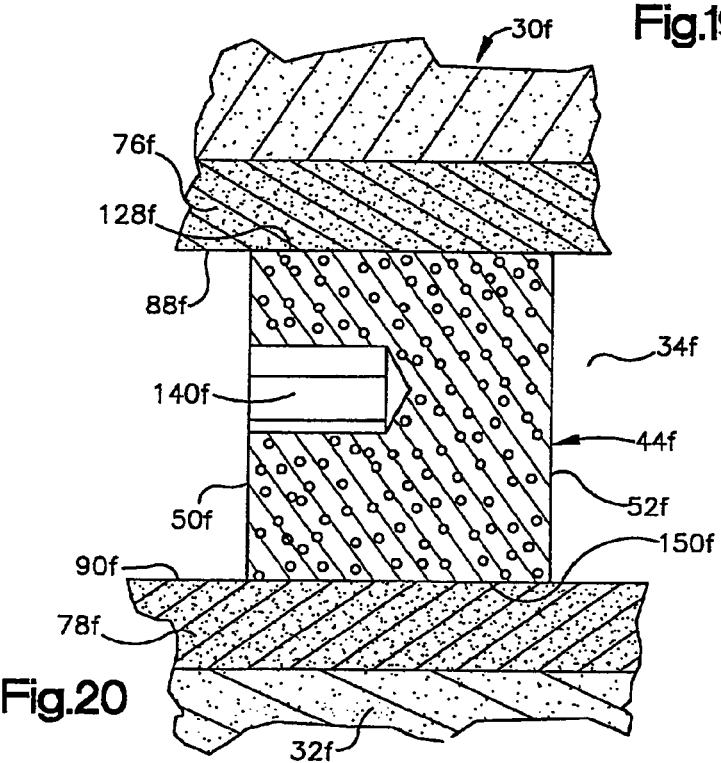

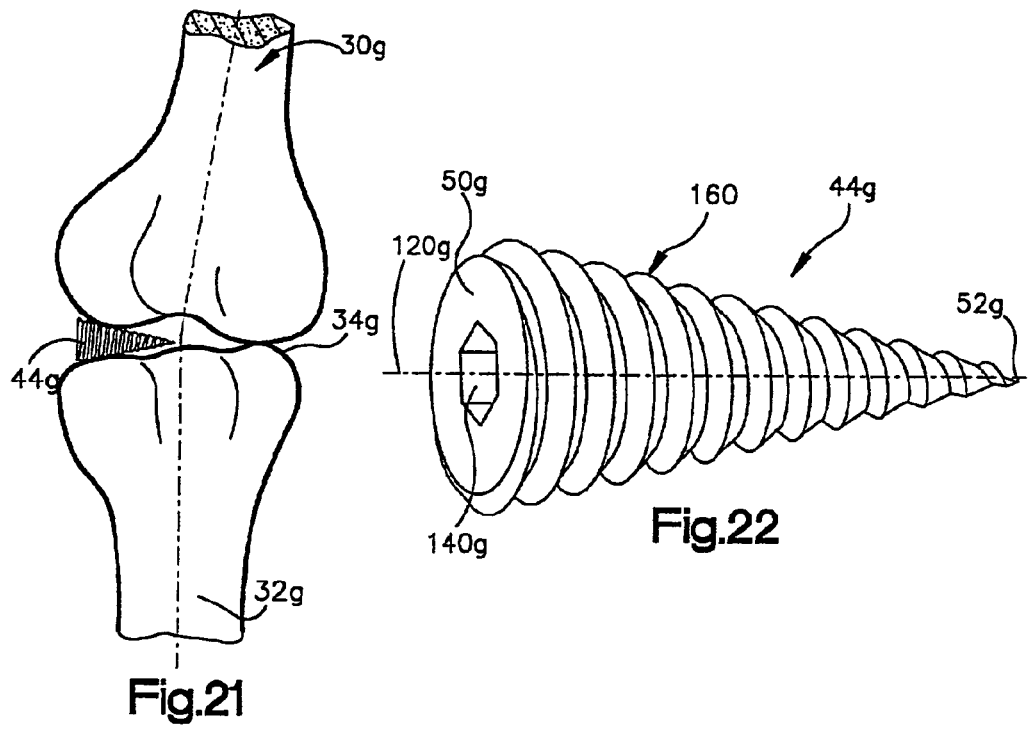
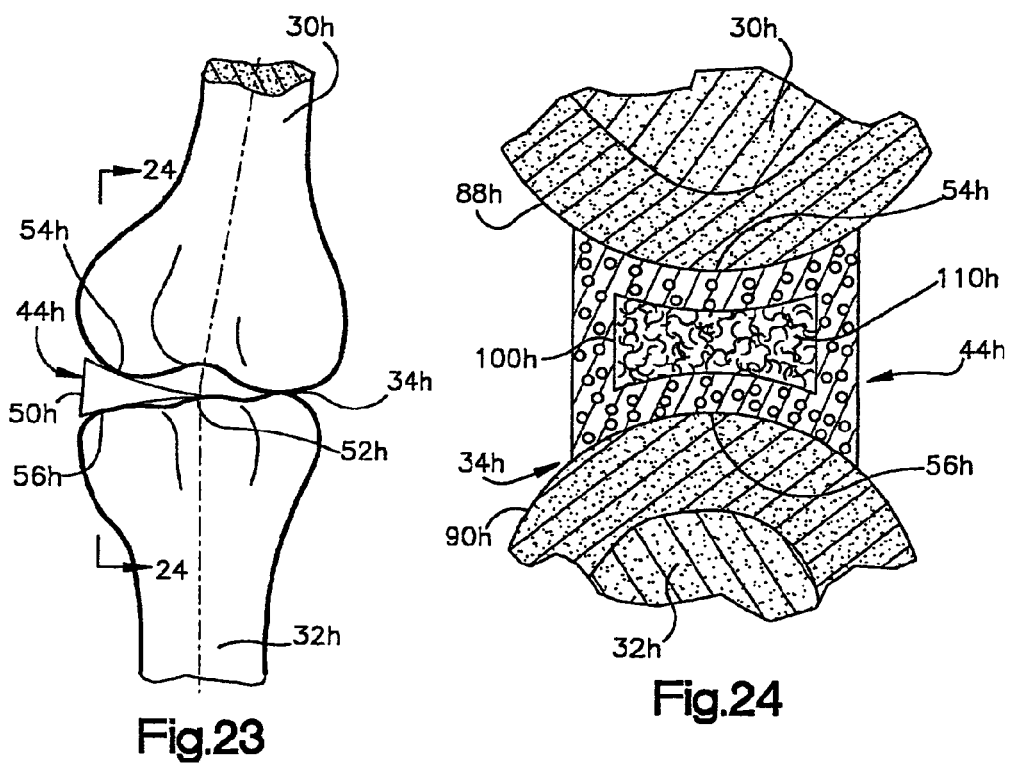

JOINT SPACER

CROSS-REFERENCE TO RELATED APPLICATION

This application is a continuation of U.S. patent application Ser. No. 10/163,480, filed on Jun. 5, 2002, now U.S. Pat. No. 7,780,670 which is a continuation of U.S. patent application Ser. No. 09/569,020, filed on May 11, 2000, now U.S. Pat. No. 6,423,063, which is a continuation of U.S. patent application Ser. No. 09/137,443, filed on Aug. 20, 1998, now U.S. Pat. No. 6,099,531.

FIELD OF THE INVENTION

The present invention relates to a new and improved method of changing a spatial relationship between bones which are interconnected at a joint in a patient's body.

BACKGROUND OF THE INVENTION

It has previously been suggested that joints between bones be fused, that is, surgically immobilized, to promote patient comfort. Thus, U.S. Pat. No. 5,026,373 suggests that a fusion cage be positioned between adjacent vertebrae. Perforations are formed in the cage. The cage is packed with a bone-inducing substance. A method for immobilizing vertebrae is also disclosed in U.S. Pat. No. 5,015,255.

It has previously been suggested that the spatial relationship between portions of a bone in a patient's body be changed to correct deformities. This may be done by removing a wedge-shaped piece of bone in the manner disclosed in U.S. Pat. No. 5,601,565.

Another method of changing the spatial relationship between portions of a bone in a patient's body includes forming a slot in the bone. A forked wedge tool is inserted into the slot. A plate is then placed in a central opening in the forked wedge tool and positioned against the bone. The plate is secured to the bone. The forked wedge tool is then removed from the opening. This method of changing the spatial relationship between portions of a bone in a patient's body is disclosed in U.S. Pat. No. 5,620,448.

A method and apparatus for use in changing a spatial relationship between portions of a bone in a patient's body is also disclosed in co-pending U.S. patent application Ser. No. 09/109,126, filed Jun. 30, 1998 by Peter M. Bonutti and entitled Method And Apparatus For Use In Operating On A Bone. This application discloses the use of a wedge member to expand a slot formed in a bone. The wedge member is porous and may be coated with and/or contain bone growth promoting material. The wedge member may have a configuration which corresponds to a configuration of a portion of the bone which is engaged by the wedge member. Alternatively, the wedge member disclosed in the aforementioned application Ser. No. 09/109,126 may have a circular cross sectional configuration with an external thread convolution to enable the wedge member to be moved into an opening in a bone by rotating the wedge member

SUMMARY OF THE INVENTION

A new and improved method and apparatus is provided to change a spatial relationship between bones which are interconnected at a joint in a patient's body. When this is to be done, an opening is formed in a portion of the patient's body to expose the joint interconnecting the bones. One of the bones is moved relative to the other by expanding at least a portion of the joint with a wedge member. The wedge member is moved into the joint and applies force against the bones. The opening is closed with the wedge member still disposed in the joint between the bones. Force is then transmitted between the bones through the wedge member to maintain the joint in an expanded condition.

If the joint is to be flexed after being expanded by the wedge member, the wedge member may be connected with only one of the bones. Alternatively, if the joint is to be immobilized (fused) after inserting the wedge member, the wedge member may be fixedly connected with the bones interconnected at the joint. The wedge member may be porous and may be coated with and/or contain bone growth promoting material.

One embodiment of the wedge member has major side surfaces extending between thick and thin end portions of the wedge member. The wedge member is moved into the joint with the thin end portion leading. As the wedge member is moved into the joint, the thick trailing end portion of the wedge member expands the joint.

In another embodiment of the invention, the wedge member is rotated relative to the joint to expand the joint. The wedge member may have a circular cross sectional configuration and an external thread convolution which extends from a thin leading end of the wedge member to a thick trailing end of the wedge member. The wedge member is pressed into the joint and rotated to cause the wedge member to expand the joint.

In another embodiment of the invention, the wedge member has surface areas which are relatively close together and other surface areas which are relatively far apart. The wedge member is moved into the joint with the surface areas which are close together engaging the adjacent bones. The wedge member is then rotated to apply force against the adjacent bones to expand the joint. The wedge member may be rotated about its central axis to apply forced against the bones and expand the joint. Alternatively, the wedge member may be rotated about a location where the wedge member engages one of the bones.

Regardless of which embodiment of the wedge member is selected, the wedge member may be used with any one of the many different bones and joints in a patient's body. The wedge member may be utilized at joints in a patient's wrist, ankle, hand, foot, back or other portions of the patient's body. The wedge member may be particularly advantageous when a joint between vertebrae in patient's back is to be immobilized. One or more wedge members may be used to expand a joint and transmit force between bones.

BRIEF DESCRIPTION OF THE DRAWINGS

The foregoing and other features of the present invention will become more apparent from the following description taken in connection with the accompanying drawings wherein:

FIG. 1 is a schematic illustration depicting the spatial relationship between bones at a joint in a patient's body;

FIG. 2 is a schematic illustration depicting the manner in which a wedge member is inserted into the joint between the bones of FIG. 1 to expand a portion of the joint and change the spatial relationship between the bones;

FIG. 3 is a schematic illustration of another embodiment of the invention in which the joint of FIG. 1 is flexed after the wedge member has been inserted into the joint and connected with only one of the bones;

FIG. 4 is a schematic illustration depicting an alternative manner of inserting the wedge member into the joint between the bones of FIG. 1;

FIG. 5 is a schematic pictorial illustration of the wedge member of FIGS. 2 and 3;

FIG. 6 is a plan view further illustrating the construction of the wedge member of FIG. 5;

FIG. 7 is a side view, taken generally along the line 7-7 of FIG. 6, of the wedge member of FIG. 5;

FIG. 9 is a fragmentary schematic sectional view, generally similar to FIG. 8, but on a reduced scale, illustrating an embodiment of the invention in which the wedge member is porous;

FIG. 10 is a fragmentary schematic sectional view, generally similar to FIG. 9, illustrating an embodiment of the wedge member which is porous and has a chamber which holds bone growth promoting material;

FIG. 11 is a fragmentary schematic sectional view, generally similar to FIGS. 8-10, illustrating the manner in which the wedge member of FIG. 3 is connected with only one bone to enable the joint between bones to be flexed;

FIG. 12 is a schematic illustration depicting the manner in which a rotatable wedge member is moved into a joint between bones;

FIG. 13 is a schematic illustration depicting the wedge member of FIG. 12 after the wedge member has been rotated to expand a portion of the joint between the bones;

FIG. 14 is an enlarged fragmentary schematic sectional view, taken generally along the line 14-14 of FIG. 12, illustrating the relationship of the rotatable wedge member to the bones prior to rotation of the wedge member;

FIG. 15 is an enlarged fragmentary schematic sectional view, taken generally along the line 15-15 of FIG. 13, illustrating the relationship of the rotatable wedge member of FIG. 14 to the bones after rotation of the wedge member;

FIG. 16 is a fragmentary schematic sectional view, taken generally along the line 16-16 of FIG. 15, illustrating the manner in which the rotatable wedge member is connected with the bones;

FIG. 18 is a fragmentary sectional view, generally similar to FIG. 14, illustrating the relationship between the bones at a joint when another embodiment of the rotatable wedge member is in the initial orientation illustrated in FIG. 12 relative to the bones;

FIG. 19 is a fragmentary schematic sectional view, generally similar to FIG. 15, illustrating the relationship of the rotatable wedge member of FIG. 18 to the bones after the wedge member has been rotated;

FIG. 20 is a fragmentary schematic sectional view, taken generally along the line 20-20 of FIG. 19, further illustrating the construction of the rotatable wedge member;

FIG. 21 is a schematic illustration, generally similar to FIG. 2, depicting the manner in which another embodiment of the rotatable wedge member is moved into a joint between bones in a patient's body;

FIG. 22 is an enlarged schematic pictorial illustration of the rotatable wedge member of FIG. 21;

FIG. 23 is a fragmentary schematic illustration, generally similar to FIG. 2, depicting the manner in which another embodiment of the wedge member is moved into a joint between bones in a patient's body; and FIG. 24 is an enlarged fragmentary schematic sectional view, taken generally along the line 24-24 of FIG. 23, further illustrating the relationship of the wedge member to the bones.

DETAILED DESCRIPTION OF THE INVENTION

General Description

Figure 8:
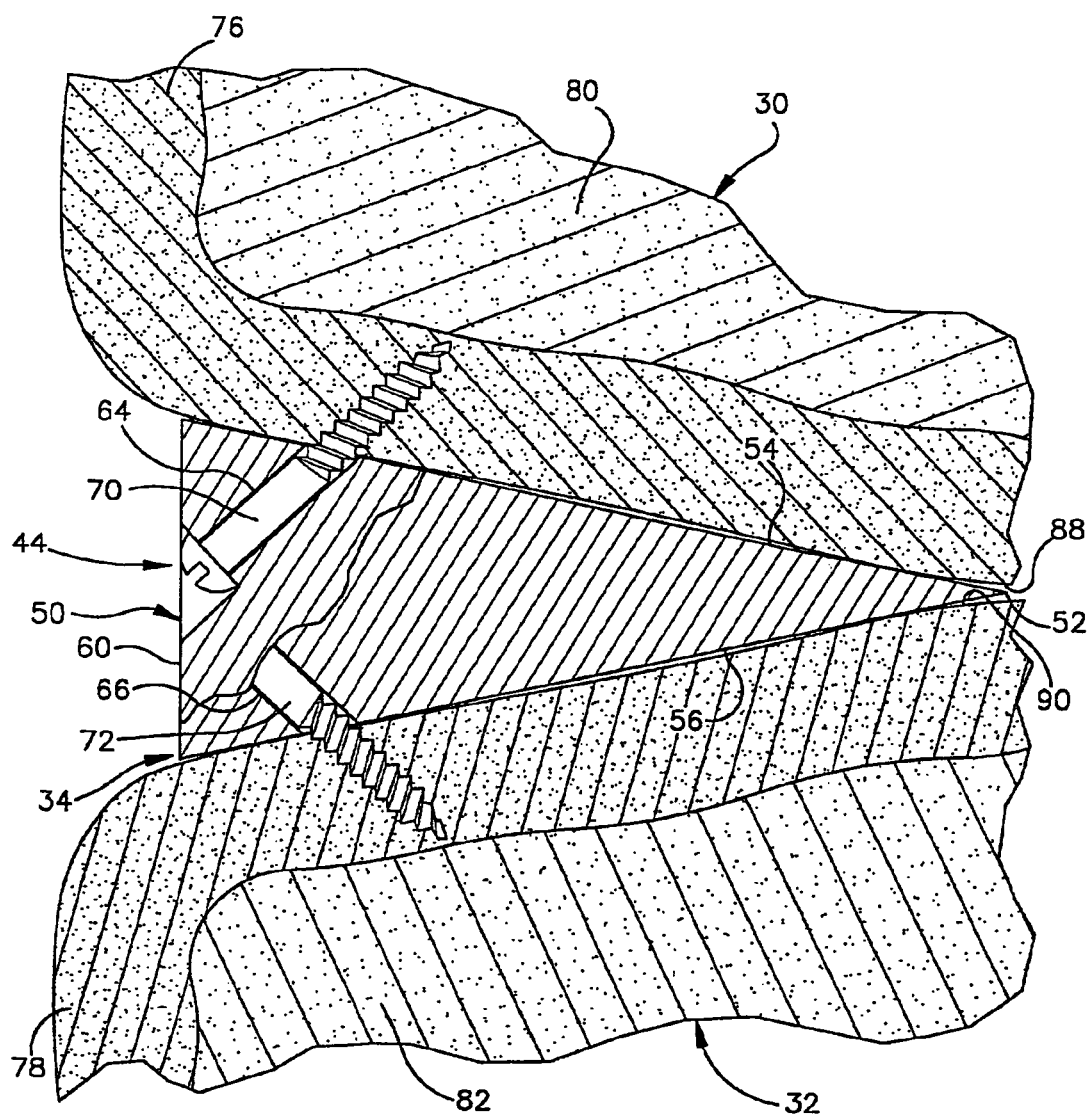
FIG. 8 is an enlarged fragmentary schematic sectional view depicting the manner in which the wedge member of FIGS. 5-7 is positioned, as shown in FIG. 2, in a joint between bones.

An upper or first bone 30 in a patient's body is illustrated schematically in FIG. 1. A lower or second bone 32 is connected with the upper bone 30 at a joint 34. The bones 30 and 32 and joint 34 have been illustrated schematically to represent any one of many bones and joints in a patient's body. Thus, the bones 30 and 32 and joint 34 may be disposed in a patient's hand, foot, back, or other portion of the patient's body. It should be understood that the bones 30 and 32 and joint 34 have been illustrated schematically in FIG. 1 as being representative of any one of the many joints in a human patient's body and it is not intended to limit the present invention to any particular joint.

In order to correct deformities, improve patient comfort or other reasons, it may be desired to change the spatial relationship between the upper and lower bones 30 and 32. Thus, it may be desired to change the angular relationship between longitudinal central axes 38 and 40 from the relationship illustrated schematically in FIG. 1 to the relationship illustrated schematically in FIG. 2.

In order to change the spatial relationship between the longitudinal central axes 38 and 40 of the bones 30 and 32, an opening is formed in a portion of the patient's body to expose the joint 34. A wedge member 44 (FIG. 2) is moved into the exposed joint 34 between the bones 30 and 32. The wedge member 44 applies force against the outer side surfaces of the bones 30 and 32 at the joint 34 to expand a portion of the joint.

As the wedge member 44 is moved into the joint 34, in the manner illustrated schematically in FIG. 2, the lower bone 32 is pivoted relative to the upper bone 30 about an axis extending through the joint 34. This changes the angular orientation of the lower bone 32 relative to the upper bone 30. Thus, the spatial relationship between the upper and lower bones 30 and 32 is changed from the spatial relationship illustrated in FIG. 1 to the spatial relationship illustrated in FIG. 2 by the wedge member 44.

In FIG. 2, the wedge member 44 has been illustrated schematically as having an extent which corresponds to approximately one-half of the extent of the joint 34. However, it is contemplated that the wedge member 44 could have an extent which is either smaller than or greater than the extent illustrated in FIG. 2. Thus, the distance between the thick and thin end portions of the tapered wedge member 44 may be less than one-half of the width of the joint 34. Similarly, the distance between the thin leading end portion and thick trailing end portion of the wedge member 44 may be greater than one-half of the width of the joint 34.

The wedge member 44 may be relatively narrow, as measured along the thin end portion of the wedge member. This would enable a plurality of narrow wedge members 44 to be used to expand a single joint 34. If the wedge member 44 is relatively wide, only a single wedge member may be required to expand a joint 34, as shown in FIG. 2.

In the embodiment of the invention illustrated in FIG. 2, the joint 34 is fused after the joint has been expanded by the wedge member 44 to change the spatial relationship between the bones 30 and 32. Thus, after the joint 34 has been expanded by the wedge member 34, the joint is immobilized with the upper and lower bones 30 and 32 in the spatial relationship illustrated in FIG. 2. When the wedge member 44 is utilized in association with joints between vertebrae in a patient's back, it is believed that it may be particularly advantageous to immobilize the joint 34.

Immobilization of the joint 34 may be accomplished by connecting the wedge member 44 with both the upper bone 30 and the lower bone 32. Immobilization of the joint 34 may also be accomplished by the growth of bone and/or other body tissue between the two bones 30 and 32 at the joint 34. Known bone growth promoting materials may be provided at the joint 34 if desired. The bone growth promoting materials may include bone morphogenic proteins and/or other osteoinductive materials.

In the embodiment of the invention illustrated in FIG. 3, the joint 34 is capable of being flexed after the wedge member 44 has been utilized to expand a portion of the joint. Thus, once the wedge member 44 has been inserted into the joint 34, in the manner illustrated in FIG. 2, the patient may flex the joint under the influence of force transmitted to the bones 32 and 30 from muscle tissue in the patient's body.

When the joint 34 is flexed, as illustrated schematically in FIG. 3, the bone 32 moves away from the wedge member 44. The wedge member 44 is fixedly connected to only the bone 30. This allows the bone 32 to move away from the wedge member. It is believed that it will be particularly advantageous to enable the joint 34 to be flexed when the wedge member is utilized to correct deformities occurring in hands, feet, wrists or ankles of a patient. However, it should be understood that the wedge member could be attached to a single bone at any joint in a patient's body which is to be flexed after the wedge member has been used to expand the joint.

In the embodiment of the invention illustrated in FIGS. 1-3, the wedge member 44 has been shown as being moved into the joint 34 in a direction which is perpendicular to an axis about which the joint is flexed. Thus, the wedge member 44 is moved into the joint 34 (FIG. 2) in a direction perpendicular to the axis about which the joint 34 is schematically illustrated in FIG. 3 as being flexed.

In the embodiment of the invention illustrated in FIG. 4, the wedge member 44 is inserted into the joint 34 in a direction parallel to the axis about which the joint is normally flexed. Thus, the wedge member 44 is illustrated in FIG. 4 as being inserted into the joint 34 in a direction perpendicular to the plane of the drawing of the joint 34 in FIGS. 1 and 3. It should be understood that the wedge member 44 could be inserted into a joint, such as the joint 34, in any desired direction in order to obtain a desired expansion of the joint. Thus, the wedge member 44 could be moved into the joint 34 along a path which is neither perpendicular to or parallel to the axis about which the joint is flexed.

After one or more wedge members 44 have been positioned in a joint 34, in the manner previously explained, the opening in the patient's body is closed. When the opening in the patient's body is closed, the wedge member 44 remains in the joint 34 between the bones 30 and 32. The wedge member 44 is formed of a rigid material which is capable of transmitting force between the bones 30 and 32 immediately after being positioned in the joint 34. Therefore, the wedge member 44 is effective to maintain the changed spatial relationship, such as the spatial relationship illustrated in FIG. 2, between the bones 30 and 32 during loading of the joint 34 immediately after positioning of the wedge member in the joint.

Wedge Member

The wedge member 44 (FIGS. 5-7) tapers from a thick end portion 50 to a thin end portion 52. The wedge member 44 has flat upper and lower major side surfaces 54 and 56 (FIG. 7) which slope toward each other from the thick end portion 50 to the thin end portion 52. The major side surfaces 54 and 56 intersect at the thin end portion 52. The pointed thin end portion 52 of the wedge member 44 facilitates moving the wedge member into the joint 34 between the bones 30 and 32 (FIG. 2).

In the illustrated embodiment of the wedge member 44 (FIGS. 5-7), the thick end portion 50 has an outer side surface 60 which forms a portion of a cylinder. The thin end portion 52 extends diametrically across the cylinder (FIG. 6). Therefore, the wedge member 44 has a semi-circular configuration. However, it should be understood that the configuration of the upper and lower major side surfaces 54 and 56 of the wedge member 44 corresponds to the configuration of the joint with which the wedge member is to be associated.

The semi-circular outer side surface 60 will, for many joints at least, have an irregular configuration other than the semi-circular configuration illustrated in FIGS. 5 and 6. This enables the outer side surface 60 to be aligned with the outer side surfaces of the bones 30 and 32 at the joint 34. Since most bones do not have outer side surfaces which form portions of a semi-circular, it is believed that in all probability, the wedge member 44 will have an outer side surface 60 with an irregular configuration rather than the semi-circular configuration illustrated in FIG. 5.

The extent of the thin end portion 52 of the wedge member 44 may be substantially less than shown in FIG. 6. Thus, the extent of the thin end portion 52 of the wedge member 44 may be less than one-half of the extent shown in FIG. 6. This would result in the major side surfaces 54 and 56 of the wedge member 44 having a generally U-shaped configuration. Parallel triangular side surfaces would extend between the outer side surface 50 of the wedge member 44 and opposite ends of the thin end portion 52. These triangular side surfaces would be spaced from opposite sides of the joint 34 when the wedge member 44 is inserted into the joint.

When the wedge member 44 has a relatively narrow, generally U-shaped configuration, a plurality of the wedge members may be inserted into a single joint 34 (FIG. 1). When a plurality of narrow wedge members 44 are used at one joint 34, the wedge members may have different configurations. Thus, the wedge members 44 may have different lengths and/or different angles between the upper and lower major side surfaces 54 and 56 of the wedge members.

The upper and lower major side surfaces 54 and 56 of the wedge member 44 slope toward each other from the thick end portion 50 to the thin end portion 52 of the wedge member. It is contemplated that a plurality of wedge members 44 having different acute angles between the upper and lower major side surfaces 54 and 56 may be provided. This would enable a surgeon to select the wedge member 44 having a desired thickness at the thick end portion 50. Thus, if a surgeon determines that a joint should be expanded to either a lesser or greater amount than would be accomplished by a wedge member having one angle, the surgeon may select a wedge member having a different angle and thickness to effect the desired expansion of the joint 34. It is also contemplated that a plurality of wedge members 44 having different widths, as measured along the thin end portion 52, may be provided.

The acute angle between the flat upper and lower major side surfaces 54 and 56 is determined by the extent to which the joint 34 is to be expanded, that is, the extent to which the spatial relationship between the bones 30 and 32 is to be changed by insertion of the wedge member 44. Of course, the specific angle provided between the upper and lower major side surfaces 54 and 56 of the wedge member 44 will vary depending upon the size of the joint with which the wedge member is used and the extent to which the spatial relationship between the bones 30 and 32 is to be changed by use of the wedge member. In addition, the length and width of the wedge member 44 inserted into a particular joint will be determined by the extent to which the joint is to be expanded and the total number of wedge members to be inserted into the joint.

It is believed that it may be desired to have the acute angle between the upper and lower major side surfaces 54 and 56 (FIG. 6) of the wedge member 44 within a range between one and thirty degrees. Although it is difficult to be certain, it is believed that it may be preferred to have the acute angle between the upper and lower major side surfaces 54 and 56 of the wedge member 44 vary within a range of five degrees to twenty degrees. It should be understood that the foregoing specific ranges of sizes for the angle between the upper and lower major side surfaces 54 and 56 of the wedge member 44 have been set forth herein for purposes of clarity of description and it is contemplated that the angle between the upper and lower major side surfaces 54 and 56 may be any one of many angles other than these specific angles.

The size of the wedge member relative to a specific joint 34 may vary depending upon the deformity to be corrected. Thus, a narrow wedge member 44 may have a thin end portion 52 (FIG. 6) with a length which is relatively small compared to the width of a joint. The thin end portion 52 of the narrow wedge member 44 could have a length of less than one fourth the distance across the joint. This would result in opposite ends of the thin end portion 52 being spaced from the periphery of the joint. It is contemplated that a plurality of narrow wedge members 44 could be used to expand a single joint.

The wedge member 44 may be formed of any one of many different known materials which are compatible with a patient's body. For example, the wedge member may be formed of human or animal bone, stainless steel, tantalum, a porous ceramic, or a polymeric material. If desired, the wedge member may be formed of a biodegradable material. However, it is preferred to have the wedge member 44 formed of a rigid material which is capable of enabling force to be transmitted through the joint 34 between the bones 30 and 32 immediately after installation of the wedge member in the joint.

In the embodiment of the invention illustrated in FIG. 2, the joint 34 is immobilized. To facilitate immobilization of the joint 34, the wedge member 44 is fixedly connected with the bone 30 and with the bone 32. To facilitate fixedly connecting the wedge member 44 with the bones 30 and 32, a pair of passages 64 and 66 are formed in the wedge member 44 (FIGS. 6 and 7). When the wedge member 44 is positioned in the joint 34 (FIG. 2), suitable fasteners, that is screws 70 and 72 extend through the passages 64 and 66 into the bones 30 and 32 in the manner indicated schematically in FIG. 8. The screws 70 and 72 engage hard cortical outer layers 76 and 78 of the bones 30 and 32. If desired, the screws 70 and 72 could extend into the relatively soft cancellous bone 80 and 82.

Although the wedge member 44 has been illustrated in FIG. 8 as being connected with the bones 30 and 32 by a pair of screws 70 and 72, it should be understood that the wedge member 44 may be connected with only one of the bones 30 or 32 by only one of the screws 70 or 72 if desired. For example, if the wedge member 44 is connected with the bone 30 by the screw 70, the joint 34 could be flexed in the manner illustrated schematically in FIG. 3, after the wedge member 44 has been moved into the joint.

Positioning of Wedge Member

When the wedge member 44 is to be inserted in to the joint 34 to change the spatial relationship between the bones 30 and 32 in the manner illustrated schematically in FIG. 2, a location for insertion of the wedge member into the joint 34 is selected by a surgeon. The specific location at which the wedge member 44 is inserted into the joint 34 to expand the joint will be selected by the surgeon as a function of the desired result from a particular operation. In addition, the size of the wedge member 44 will be selected by the surgeon as a function of the joint and the result to be obtained from a particular operation.

The configuration of the wedge member 44 will be selected by the surgeon as a function of the location where the wedge member is to be inserted into the joint 34. The wedge member 44 may be relatively wide and have a long thin end portion 52, as shown in FIG. 6, to enable the thin end portion to extend between opposite sides of the joint. Alternatively, the wedge member 44 may be relatively narrow and have a thin end portion 52 which is short. If this is done, the thin end portion 52 would not extend between opposite sides of the joint 34. A plurality of the narrow wedge members 44 may be inserted into a single joint 34 to expand the joint and transmit force between the bones 30 and 32.

The surgeon makes an incision in soft body tissue surrounding the joint 34 to expose the joint. Once the joint 34 has been exposed, the thin end portion 52 (FIGS. 5 and 6) of the wedge member 44 is moved into the joint 34. When the wedge member 44 is to be inserted into a joint in the manner illustrated schematically in FIG. 2, the longitudinal central axis of the thin end portion 52 of the wedge member is aligned with an axis about which the joint pivots. The wedge member is then moved into the joint 34 along a linear path which extends perpendicular to the axis about which the joint pivots. The wedge member 44 is moved into the joint 34 by applying force against the trailing thick end portion 50 of the wedge member.

As the wedge member 44 is moved into the joint 34, the upper major side surface 54 (FIGS. 5 and 7) of the wedge member slides along an outer side surface 88 (FIG. 8) of the outer layer 76 of hard cortical bone. The lower major side surface 56 of the wedge member 44 slides along an outer side surface 90 of the outer layer 78 of hard cortical bone.

The outer side surfaces 88 and 90 of the bones 30 and 32 are in their naturally occurring conditions. Thus, the outer side surfaces 88 and 90 of the bones 30 and 32 are not cut away to prepare for insertion of the wedge member 44 into the joint 34. However, it should be understood that under certain circumstances that it may be necessary to abrade or otherwise cut the outer side surfaces 88 and 90 of the outer layers 76 and 78 of hard cortical bone to prepare the joint 34 for insertion of the wedge member 44.

As the thin leading end portion 52 (FIG. 8) of the wedge member 44 moves into the joint 34, the upper and lower major side surfaces 54 and 56 apply force against the outer side surfaces 88 and 90 on the bones 30 and 32. As this occurs, the joint 34 is expanded. As the joint 34 is expanded, the bone 32 is pivoted, relative to the bone 30, from the initial orientation, shown in FIG. 1, to the improved orientation shown in FIG. 2. As this occurs, the longitudinal central axis 40 of the bone 32 moves relative to the longitudinal central axis 38 of the bone 30. Therefore, the angular relationship between the bones 30 and 32 is changed by expansion of a portion of the joint 34 by insertion of the wedge member 44 into the joint.

When the wedge member 44 has been pressed the desired distance into the joint 34, by the application of force against the thick end portion 50 of the wedge member 44, the outer side surface 60 on the wedge member moves slightly inward of the outer side surfaces on the bones 30 and 32 (FIG. 8). The outer side surface 60 on the wedge member 44 has a configuration which corresponds to the configurations of the outer side surfaces on the bones 30 and 32 adjacent to the joint 34. Therefore, the wedge member 44 does not project outward from the joint. This minimizes any tendency of the wedge member to subsequently abrade body tissue adjacent to the joint 34.

Once the wedge member 44 has been moved into the desired orientation relative to the bones 30 and 32, as illustrated schematically in FIG. 8, the wedge member 44 is fixedly connected with the bones 30 and 32 by the screws 70 and 72 to immobilize the joint. The area surrounding and directly adjacent to the wedge member 44 is packed with bone growth promoting material and/or bone chips. The bone growth promoting materials may include bone morphogenic proteins and/or other osteoinductive materials. This promotes fusion of the bones 30 and 32 for remedial immobilization of the joint 34.

Since the wedge member 44 is rigid, it can immediately transmit loads between the bones 30 and 32. Therefore, after the incision which exposed the joint 34 has been closed, the patient can begin to load the joint 34. The wedge member 44 is effective to maintain the joint 34 in an expanded condition during loading of the joint. Therefore, the bones 30 and 32 remain in the improved spatial relationship illustrated in FIG. 2 during loading of the joint 34.

Wedge Member—Second Embodiment

In the embodiment of the invention illustrated in FIGS. 1-8, a solid wedge member has been utilized to expand the joint 34. In the embodiment of the invention illustrated in FIG. 9, a porous wedge member is utilized to expand a joint. Since the embodiment of the invention illustrated in FIG. 9 is generally similar to the embodiment of the invention illustrated in FIGS. 1-8, similar numerals will be utilized to designate similar components, the suffix letter "a" being associated with the numerals of FIG. 9 in order to avoid confusion.

A wedge member 44a is positioned in a joint 34a between bones 30a and 32a. The wedge member 44a engages outer side surfaces 88a and 90a on layers 76a and 78a of hard cortical bone. The outer side surfaces 88a and 90a are in their naturally occurring conditions.

As the wedge member 44a is moved into the joint 34a, flat upper and lower major side surfaces 54a and 56a on the wedge member 44a slide along the outer side surfaces 88a and 90a on the bones 30a and 32a. The upper and lower major side surfaces 54a and 56a of the wedge 44a apply force against the outer side surfaces 88a and 90a of the bones 30a and 32a to expand the joint 34a as the wedge member is moved into the joint. The wedge member 44a is moved into the joint 34a under the influence of force applied against an outer side surface 60a on a trailing thick end portion 50a of the wedge member 44a.

Once the joint 34a has been expanded to change the spatial relationship between the bones 30a and 32a, suitable fasteners (screws) 70a and 72a are inserted through passages in the wedge member 44a. The screws 70a and 72a engage the hard cortical outer layers 76a and 78a of bone to fixedly secure the wedge member 44a with the bones 30a and 32a. With further reference to FIGS. 8-9, it may be seen that passage 64 widens proximate end portion 50a configured to receive a head of fastener 70a that is wider than a shaft of the fastener.

A single wedge member 44a is used to expand the joint 34a. However, a plurality of narrow wedge members 44a may be inserted into the joint at spaced apart locations about the periphery of the joint if desired.

In accordance with a feature of this embodiment of the invention, the wedge member 44a is porous so that bone can grow through the wedge member. It is contemplated that the wedge member could be provided with a porous construction by having passages extend through the wedge member between the upper and lower major side surfaces 54a and 56a of the wedge member. The open ends of the passages would enable bone to grow through the wedge member 44a.

In the embodiment of the wedge member 44a illustrated in FIG. 9, the wedge member is formed of a rigid open cell material. The open cell material provides cavities in which bone can grow through the wedge member 44a. Thus, the wedge member 44a (FIG. 9) has a cellular construction similar to coral.

It is contemplated that the wedge member 44a may be coated with a material which promotes the growth of bone. The cells in the wedge member 44a may be at least partially filled with bone growth promoting material. The bone growth promoting materials may be bone morphogenic proteins and other osteoinductive materials. In addition to bone growth promoting material associated with the wedge member 44a, the space around and adjacent to the wedge member 44a in the joint 34a may be packed with bone growth promoting material and/or bone chips.

The wedge member 44a is rigid and can be subject to normal loading immediately after being positioned in the joint 34a. This enables the patient to subject the bones 30a and 32a to normal loading without waiting for fusion to occur through and around the wedge member 44a. Of course, with the passage of time, the growth of bone through the wedge member 44a and around the wedge member will strengthen the immobilization of the joint 34a.

In the embodiment of the invention illustrated in FIG. 9, the passages through the wedge member 44a are formed by the open cell structure of the wedge member This results in the passages through the wedge member 44a having an irregular configuration. If desired, linear passages could be formed in the wedge member 44a. The linear passages may be drilled, cast, or formed in other ways in the wedge member 44a.

Hollow Wedge Member

In the embodiment of the invention illustrated in FIGS. 1-8, the wedge member 44 is formed by a solid piece of material. In the embodiment of the invention illustrated in FIG. 9, the wedge member 44a is formed by a continuous piece of porous material. In the embodiment of the invention illustrated in FIG. 10, the wedge member is formed by a hollow piece of porous material. Since the embodiment of the invention illustrated in FIG. 10 is generally similar to the embodiments of the invention illustrated in FIGS. 1-9, similar numerals will be utilized to designate similar components, the suffix letter "b" being associated with the numerals of FIG. 10 to avoid confusion.

In the embodiment of the invention illustrated in FIG. 10, a wedge member 44b is inserted into a joint 34b between bones 30b and 32b to expand the joint. Expansion of the joint 34b by the wedge member 44b changes the spatial relationship between the bones 30b and 32b. The wedge member 44b is held against movement relative to the bones 30b and 32b by fasteners (screws) 70b and 72b. The fasteners 70b and 72b extend through passages in the wedge member 44b into layers 76b and 78b of hard cortical bone on bones 30b, 32b. The layers 76b and 78b are in their naturally occurring condition.

When the wedge member 44b is to be moved into the joint, a thin end portion 52b of the wedge member 44b is pressed into the joint 34b by applying force against an outer side surface 60b at a thick end portion 50b of the wedge member 44b. The force applied against the trailing thick end portion 50b of the wedge member 44b causes flat upper and lower major side surfaces 54b and 56b to slide along outer side surfaces 88b and 90b. As the upper and lower major side surfaces 54b and 56b on the wedge member 44b slide along the outer side surfaces 88b and 90b of the bones 30b and 32b, the wedge member applies force against the bones to expand the joint 34b in the manner previously explained.

In accordance with a feature of this embodiment of the invention, the wedge member 44b (FIG. 10) is hollow. Therefore, a compartment or cavity 100 is formed in the wedge member 44b. The compartment 100 has upper and lower inner side surfaces 102 and 104 which are smaller than the upper and lower major side surfaces 54b and 56b of the wedge member 44b. However, the inner side surfaces 102 and 104 of the compartment 100 have the same general configuration as the upper and lower major side surfaces 54b and 56b of the wedge member 44b.

The compartment 100 is filled with bone growth inducing material 110. The bone growth inducing material 110 is positioned in the compartment 100 through a suitable opening (not shown) formed in either the upper major side surface 54b or the lower major side surface 56b of the wedge member 44b. Once the compartment 100 has been filled with bone growth inducing material 110, the opening to the compartment is closed. However, the wedge member 44b is formed of a porous material which enables bone to grow through the wedge member.

The growth of bone through the wedge member 44b is promoted by the bone growth inducing material 110 in the compartment 100. The bone growth inducing material 110 in the compartment 100 may be any of many known bone morphogenic proteins and osteoinductive materials. For example, apatite compositions with collagen may be utilized. Demineralized bone powder may also be utilized. Regardless of which of the known bone growth inducing materials are selected, the presence of the bone growth promoting material 110 in the compartment 100 will promote a growth of bone through openings in the porous wedge member 44b.

The wedge member 44b may, itself, be formed of a suitable rigid material, such as tantalum, stainless steel, or ceramic materials. In addition to the bone growth inducing material 110, the surfaces of the wedge member 44b and openings in the porous material of the wedge member may be coated with suitable bone growth promoting materials.

The wedge member 44b is porous so that bone can grow through the wedge member. In the embodiment of the invention illustrated in FIG. 10, the wedge member is formed of an open cell material having a construction similar to coral. The open cell material provides irregular passages which extend through the wedge member 44b and enable the bone to grow through the wedge member. However, it should be understood that the wedge member 44b could be formed of a solid material with passages drilled or cast in the wedge member. Regardless of which of the materials the wedge member is formed, it is believed that it will be advantageous to have the material be sufficiently rigid to enable the joint 44b to be load bearing immediately after an operation installing the wedge member in the joint.

Single Connection for Wedge Member

In the embodiments of the invention illustrated in FIGS. 8-10, the wedge members 44, 44a, and 44b are connected with bones on opposite sides of a joint by suitable fasteners (screws). In the embodiment of the invention illustrated in FIG. 11, the wedge member is connected with only one of the bones. Since the embodiment of the invention illustrated in FIG. 11 is generally similar to the embodiments of the invention illustrated in FIGS. 1-10, similar numerals will be utilized to designate similar components, the suffix letter "c" being associated with the numerals of FIG. 11 to avoid confusion.

A wedge member 44c is inserted into a joint 34c between upper and lower bones 30c and 32c. The wedge member 44c has the same general configuration and construction as the wedge member 44 of FIGS. 5-8. However, the wedge member 44c is connected with only one of the bones 30c and 32c. Thus, rather than utilizing a pair of fasteners to secure the wedge member 44c to the upper and lower bones 30c and 32c, only a single fastener 70c is utilized to connect the wedge member 44c with the upper bone 30c. Therefore, installation of the wedge member 44c in the joint 34c does not result in immobilization of the joint.

Since the wedge member 44c is connected with the bone 30c by the fastener 70c, the bone 32c may be moved away from the wedge member during flexing of the joint 34c. This may result in the upper major side surface 54c on the wedge member 54c remaining in engagement with the outer side surface 88c on the bone 30c while the outer side surface 90c on the bone 32c moves away from the lower major side surface 56c on the wedge member 44c. Of course, a single fastener 70c may be utilized to hold the wedge member in the joint 34c where the outer side surfaces 88c and 90c on the upper and lower bones 30c and 32c remain in engagement with the upper and lower major side surfaces 54c and 56c of the wedge member 44c.

In the embodiment of the wedge member 44c illustrated in FIG. 11, the wedge member is formed of a solid material through which bone does not grow. However, it is contemplated that a single fastener, corresponding to the fastener 70c of FIG. 11, may be used to connect a porous wedge member with a bone. Of course, bone may grow through the porous wedge member. The porous wedge member may have the same construction as shown in FIGS. 9 and 10, with the exception of being held in place by only a single fastener 70c.

Rotatable Wedge Member

In the embodiment of the invention illustrated in FIGS. 1-11, the wedge member 44 is moved into the joint 34 between the upper and lower bones 30 and 32 along a linear path. The wedge member 44 is moved into the joint 34 with the thin end portion 52 of the wedge member leading and the thick end portion 50 of the wedge member trailing. The tapered configuration of the wedge member results in the application of force against the upper and lower bones 30 and 32 to expand the joint 34 in the manner previously explained.

In the embodiment of the invention illustrated in FIGS. 12-16, the wedge member is moved into the joint between the upper and lower bones and then rotated. During initial movement of the wedge member into the joint between the bones, there may be some expansion of the joint. During rotation of the wedge member in the joint, there is further expansion of the joint. Since the embodiment of the invention illustrated in FIGS. 12-15 is generally similar to the embodiments of the invention illustrated in FIGS. 1-11, similar numerals will be utilized to designate similar components, the suffix letter "d" being associated with the numerals of FIGS. 12-15 to avoid confusion.

Upper and lower bones 30d and 32d are interconnected at a joint 34d (FIG. 12). Prior to insertion of a wedge member 44d, the upper and lower bones 30d and 32d are in the same spatial orientation relative to each other as is illustrated in FIG. 1. Upon insertion of the wedge member 44d into the joint 34d, in the manner illustrated in FIG. 12, there may be a slight expansion of the joint 34d and a slight change in the orientation of the upper bone 30d relative to the lower bone 32d. There is a relatively small change in the spatial relationship between the upper bone 30d and the lower bone 32d because the wedge member 44d is inserted into the joint 34d in an orientation in which the wedge member 44d is relatively thin as viewed in FIG. 12, that is, in a direction transverse to the joint 34d.

After the wedge member 44d has been inserted into the joint 34d in the manner indicated schematically in FIG. 12, the wedge member 44d is rotated, through less than one revolution, about an axis 120 in the manner indicated schematically by an arrow 122 in FIG. 13. As the wedge member 44d is rotated through approximately ninety degrees about the axis 120, the wedge member applies force against the upper and lower bones 30d and 32d to expand the joint 34d. As the joint 34d is expanded by rotation of the wedge member 44d, the spatial relationship between the upper and lower bones 30d and 32d changes from the spatial relationship illustrated schematically in FIG. 12 to the spatial relationship illustrated schematically in FIG. 13. Thus, by the combined effect of insertion of the wedge member 44d into the joint 34d and rotation of the wedge member in the joint, the spatial relationship of the upper and lower bones 30d and 32d was changed from the spatial relationship illustrated in FIG. 1 for the bones 30 and 32 to the spatial relationship illustrated in FIG. 13 for the upper and lower bones 30d and 32d.

The bones 30d and 32d illustrated schematically in FIGS. 12 and 13 should be considered as being representative of bones at many different locations in a patient's body. Thus, the bones 30d and 32d may be any of the many bones in a patient's wrist, ankle, hand, foot, back, or other portion of a patient's body. The bones 30d and 32d may be vertebrae in a patient's back. It should be understood that the wedge member 44d may be used with any one of the many different types of joints in a patient's body.

The wedge member 44d has a generally oval, cross-sectional configuration (FIGS. 14 and 15), as viewed in a plane perpendicular to a longitudinal central axis of the wedge member. Thus, the wedge member 44d has an outer side surface 126 (FIG. 14) with a pair of arcuate nose portions 128 and 130. The arcuate nose portions 128 and 130 of the outer side surface 126 are interconnected by a pair of arcuate side portions 134 and 136.

The arcuate outer side surface 126 tapers from a thick end portion 50d (FIG. 16) to a thin end portion 52d. In the illustrated embodiment of the wedge member 44d, the thin end portion 52d is blunt or truncated. Thus, the thin end portion 52d of the wedge member 44d does not come to a sharp point as does the thin end portions of the wedge members 44, 44a, 44b and 44c.

It should be understood that the wedge members 44a, 44b and 44c (FIGS. 5-11) could be constructed with a blunt thin end portion corresponding to the blunt thin end portion 52d (FIG. 16) on the wedge member 44d if desired. However, it is believed that by having the thin end portion of the wedge members of FIGS. 5-11 taper to a sharp point, insertion of the wedge members into a joint is facilitated. Similarly, if desired, the wedge member 44d could be provided with a thin end portion 52d (FIG. 16) which comes to a sharp point in the same manner as the wedge members 44, 44a, 44b and 44c.

When the wedge member 44d is inserted into the joint 34d (FIG. 14), the arcuate side portion 134 engages the outer side surface 88d of the upper bone 30d and the arcuate side portion 136 engages the outer side surface 90d of the lower bone 32d. The arcuate side portions 134 and 136 are relatively close together so that minimal expansion of the joint 34d occurs when the wedge member 44d is inserted into the joint. As the wedge member 44d is inserted into the joint 34d, the arcuate side portions 134 and 136 slide along and are effective to apply force against the outer side surfaces 88d and 90d of the upper and lower bones 30d and 32d to effect some expansion of the joint 34d. The outer side surfaces 88d and 90d of the bones 30d and 32d are in their naturally occurring conditions.

After the wedge member 44d has been inserted into the joint 34d, in the manner shown in FIGS. 12 and 14, a suitable tool is inserted into a hexagonal socket 140 (FIG. 14) in the wedge member 44d. Torque is transmitted from the tool to the wedge member 44d to rotate the wedge member through less than one revolution in the direction indicated by the arrow 122 in FIGS. 13 and 15. This results in the wedge member 44d being rotated through approximately ninety degrees in a clockwise direction from the position shown in FIG. 14 to the position shown in FIG. 15. As the wedge member 44d is rotated, the wedge member applies force against the upper and lower bones 30d and 32d and expands the joint 34d.

Upon initiation of rotation of the wedge member 44d from the position shown in FIG. 14 toward the position shown in FIG. 15, the arcuate side portions 134 and 136 slide along the outer side surfaces 88d and 90d on the bones. As the rotation of the wedge member 44d continues, the arcuate nose portions 128 and 130 of the wedge member 44d approach the outer side surfaces 88d and 90d of the upper and lower bones 30d and 32d. As this is occurring, the joint 34d is expanded by the force applied against the upper and lower bones 30d and 32d by the wedge member 44d. When the wedge member 44d reaches the position shown in FIG. 15, the arcuate nose portions 128 and 130 engage the outer side surfaces 88d and 90d on the upper and lower bones 30d and 32d to hold the joint 34d in the expanded condition illustrated in FIGS. 15 and 16.

A pair of mounting tabs 144 and 146 (FIG. 16) are integrally formed with the wedge member 44d. The mounting tabs 144 and 146 project outwardly from the end portion 50d of the wedge member 44d. The mounting tabs 144 and 146 are aligned with the arcuate nose portions 128 and 130 of the outer side surface 126 on the wedge member 44d. Therefore, the mounting tabs 144 and 146 are disposed adjacent to the bones 30d and 32d in the manner illustrated schematically in FIG. 16.

A pair of retaining screws 70d and 72d extend through the mounting tabs 144 and 146 into the outer layers 76d and 78d of hard cancellous bone on the upper and lower bones 30d and 32d. The mounting screws or fasteners 70d and 72d are effective to hold the wedge member 44d against rotation relative to the upper and lower bones 30d and 32d. Bone growth promoting material and/or bone chips may be packed in the joint 34d around the wedge member 44d. The wedge member 44d is rigid and can transmit force between the bones 30d and 32d as soon as it is rotated to the position shown in FIGS. 15 and 16.

As is perhaps best seen in FIG. 15, the wedge member 44d is narrower than the distance across the joint 34d. Therefore, a plurality of wedge members 44d may be utilized to hold the joint 34d in the expanded condition of FIGS. 15 and 16. The plurality of wedge members 44d could be positioned in the joint 34d with their rotational axes 120 (FIG. 16) in a parallel relationship or with their rotational axes 120 skewed relative to each other. If a plurality of wedge members 44d are utilized, they could be of different sizes or have different angles of taper along the axis 120.

It should be understood that the wedge members 44, 44a, 44b and 44c of FIGS. 5-11 could also be relatively narrow. A plurality of wedge members of FIGS. 5-11 could be positioned in a joint with their longitudinal axes either parallel or skewed relative to each other.

Porous Rotatable Wedge Member

Figure 17:
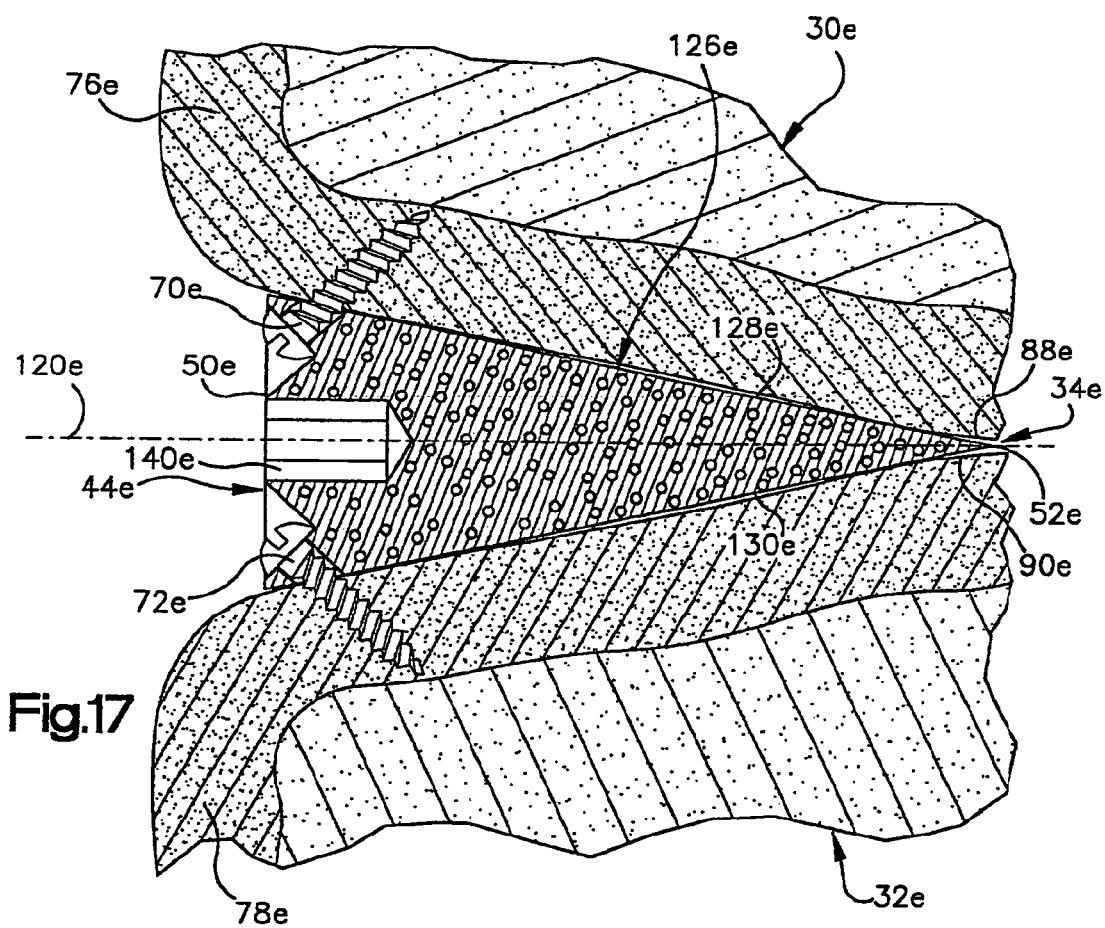
FIG. 17 is a fragmentary schematic sectional view, generally similar to FIG. 16, illustrating an embodiment of the rotatable wedge member which is porous.

In the embodiment of the invention illustrated in FIGS. 12-16, the wedge member 44d is formed as a solid body of rigid material, such as stainless steel. The wedge member in the embodiment of the invention illustrated in FIG. 17 is formed of a rigid porous material. Since the embodiment of the invention illustrated in FIG. 17 is generally similar to the embodiments of the invention illustrated in FIGS. 1-16, similar numerals will be utilized to designate similar components, the suffix letter "e" being associated with the numerals of FIG. 17 to avoid confusion.

The wedge member 44e is disposed in a joint 34e between upper and lower bones 30e and 32e. The wedge member 44e applies force against the outer side surfaces 88e and 90e of the upper and lower bones 30e and 32e to expand the joint 34e and change the orientation of the upper and lower bones relative to each other. In the embodiment of the invention illustrated in FIG. 17, the wedge member 44e tapers from a thick end portion 50e to a thin end portion 52e. In the illustrated embodiment of the invention, the thin end portion 52e of the wedge member 44e has a pointed configuration rather than the blunt configuration of the wedge member 44d of FIG. 16. However, the wedge member 44e could have the same configuration as the wedge member 44d if desired.

The wedge member 44e (FIG. 17) has an oval cross sectional configuration, as viewed on a plane extending perpendicular to a central axis 120e of the wedge member 44e. Thus, the wedge ember 44e has an outer side surface 126e with arcuate nose portions 128e and 130e. The arcuate nose portions 128e and 130 are interconnected by arcuate side portions corresponding to the arcuate side portions 134 and 136 of the wedge member 44d (FIGS. 14 and 15). A socket 140e (FIG. 17) is provided in the wedge member 44e to facilitate the application of torque to the wedge member.

In accordance with a feature of the embodiment of the invention illustrated in FIG. 17, the wedge member 44e is formed of a rigid porous material having an open cell construction. The porous open cell construction of the wedge member 44e enables bone to grow through the wedge member. The wedge member 44e may have an open cell construction similar to the construction of coral.

The wedge member 44e may be coated with bone growth promoting materials to promote the growth of bone through the wedge member. The open cells in the porous wedge member 44e could be at least partially filled with the bone growth promoting material. In addition, bone growth materials and/or bone chips may be packed in the joint 34e around the wedge member 44e. The bone growth promoting materials may include bone morphogenic proteins and/or other osteoinductive materials.

A pair of fasteners 70e and 72e are provided to connect the wedge member 44e with the upper and lower bones 30e and 32e. Thus, the fasteners 70e extends into the outer layer 76e of hard cortical bone on the upper bone 30e. Similarly, the fastener 72e extends into the outer layer 78e of hard cortical bone on the lower bone 32e. In the illustrated embodiment of the invention, the fasteners 70e and 72e extend through passages in the wedge member 44e into the upper and lower bones 30e and 32e. However, if desired, the wedge member 44e could be provided with mounting tabs, similar to the mounting tabs 144 and 146 of FIG. 16.

When the wedge member 44e is to be used to change the spatial relationship between the upper and lower bones 30e and 32e, the wedge member is inserted into the joint 34e with the arcuate nose portions 128e and 130e of the wedge member spaced from the outer side surfaces 88e and 90e on the upper and lower bones 30e and 32e. At this time, the wedge member 44e is in the same orientation as is illustrated in FIG. 14 for the wedge member 44d. Arcuate side portions of the arcuate outer side surface 126e on the wedge member 44e engage the outer side surfaces 88e and 90e on the upper and lower bones 30e and 32e in the same manner as is illustrated for the wedge member 44d in FIG. 14.

Although inserting the wedge member 44e into the joint 32e may effect an initial, relatively small expansion of the joint, the majority of the expansion of the joint 34e is obtained by rotating the wedge member 44e about its central axis 120e. To rotate the wedge member 44e about its central axis 120e, a suitable tool is inserted into the socket 140e. Force is transmitted from the tool to the wedge member 44e to rotate the wedge member. As the wedge member is rotated relative to the upper and lower bones 30e and 32e, the wedge member further expands the joint 34e and effects further change in the spatial relationship between the upper and lower bones 30e and 32e.

Once the wedge member 44e has been moved to the position illustrated in FIG. 17, that is, to a position corresponding to the position of the wedge member 44d in FIG. 15, the wedge member is connected to the upper and lower bones 30e and 32e. To connect the wedge member with the upper and lower bones 30e and 32e, the screws 70e and 72e are inserted through passages in the wedge member into the bone. Bone growth promoting material and/or bone chips may be packed in the joint 34e around the wedge member 44e.

Although a single wedge member 44e is utilized to expand the joint 34e, a plurality of wedge members could be utilized if desired. When a plurality of wedge members 34e are held to expand the joint 34e, the wedge members may all be of the same size and configuration or may have different sizes and configurations.

Rotatable Wedge Member Alternative—Embodiment

The wedge members 44d and 44e are rotated about their central axes 120d and 120e (FIGS. 16 and 17) to effect expansion of the joints 34d and 34e. In the embodiment of the invention illustrated in FIGS. 18 through 20, the wedge member is rotated about a location where the wedge member engages one of the bones. Since the embodiment of the invention illustrated in FIGS. 18-20 is generally similar to the embodiments of the invention illustrated in FIGS. 1-17, similar numerals will be utilized to designate similar components, the suffix letter "f" being associated with the numerals of FIGS. 18-20 to avoid confusion.

Upper and lower bones 30f and 32f are interconnected at a joint 34f. A wedge member 44f is illustrated inserted into the joint 34f between the upper and lower bones 30f and 32. The wedge member 44f is positioned in the joint 34f (FIG. 18) with a relatively narrow width of the wedge member between outer side surfaces 88f and 90f on hard cortical outer layers 76f and 78f of the upper and lower bones 30f and 32f. Although the outer side surfaces 88f and 90f of the upper and lower bones 30f and 32f are in their naturally occurring conditions, it is contemplated that a surgeon may want to prepare the surfaces of the bone for the wedge member 44f by cutting away extraneous material to promote seating of the wedge member 44f on the upper and lower bones 30f and 32f.

The wedge member 44f has an arcuate nose portion 128f and a pivot end portion 150f. The nose portion 128f and pivot end portion 150f are interconnected by side portions 134f and 136f. The side portion 134f has a continuously curving arcuate configuration. The side portion 136f may have a linear configuration.

The side portion 136f has a relatively flat area which engages the outer side surface 90f on the lower bone 32f when the wedge member 44f is oriented as illustrated in FIG. 18 If desired, the side portion 136f could have an arcuate configuration corresponding to the arcuate configuration of the side portion 134f. If the side portion 136f had the same configuration as the side portion 134f, the wedge member 44f would have a symmetrical configuration about an axis extending through the relatively sharply defined pivot end portion 150c.

The wedge member 44f has the same size and configuration throughout its length. Thus, the end portion 150f of the wedge member is the same size as the end portion 52f (FIG. 20). However, if desired, the wedge member 44f could taper from a relatively thick end portion 50f to a relatively thin or small end portion 52f in the manner illustrated in FIGS. 16 and 17 for the wedge members 44d and 44e. It should be understood that any one of the wedge members illustrated in FIGS. 1 through 17 could be formed with the same configuration as the wedge member 44f if desired. However, it is believed that in most instances it will probably be preferred to provide the wedge members of FIGS. 1-17 with an axially tapered configuration to facilitate insertion of the wedge members into the joint between the upper and lower bones.

The wedge member 44f (FIGS. 18, 19 and 20) is formed of a rigid porous open cell material. The rigid porous open cell material of the wedge member 44f has a construction generally similar to coral. However, the wedge member 44f could be formed of a nonporous material if desired.

It is contemplated that the wedge member 44f, like the wedge members illustrated in FIGS. 1-17, may be formed of human or animal bone, metal, ceramic, or a polymeric material. While it may be preferred to form the wedge member 44f of a porous material to enable bone to grow through the wedge member, the wedge member 44f may be formed of a solid material through which bone can not grow.

The wedge member 44f may be coated with or packed with bone growth promoting materials. The bone growth promoting materials may be bone morphogenic proteins and/or other osteoinductive materials. Bone chips may be included with the bone morphogenic proteins and/or other osteoinductive materials packed around the wedge member 44f.

Of course, the wedge member 44f may be provided with a tapered configuration to facilitate insertion into the joint 34f. When the wedge member 44f is to be utilized to change the spatial relationship between the upper and lower bones 30f and 32f, the wedge member is inserted into the joint 34f. The illustrated embodiment of the wedge member 44f has the same size and configuration throughout its length. Therefore, the wedge member 44f does not taper to a thin end portion to facilitate insertion of the wedge member into the joint 34f. Therefore, the joint 34f may be initially expanded with a suitable tool to enable the wedge member 44f to be inserted into the joint, in the orientation illustrated in FIG. 18.

When the wedge member 44f is inserted into the joint 34f, there will be a slight initial expansion of the joint. As was previously mentioned, the wedge member 44f may have an axially tapered configuration, similar to the configuration of the wedge members 44d and 44e (FIGS. 16 and 17), to facilitate insertion of the wedge member 44f into the joint 34f.

As the wedge member 44f is initially inserted into the joint 34f, the side portions 134f and 136f on the wedge member 44f slide along the outer side surfaces 88f and 90f on the upper and lower bones 30f and 32f. At this time, the arcuate nose portion 128f of the wedge member 44f is spaced from the outer side surface surfaces 88f and 90f of the upper and lower bones 30f and 32f.

To further change the spatial relationship between the upper and lower bones 30f and 32f, the wedge member 44f is rotated about an axis extending through a location where the pivot end portion 150f of the wedge member 44f engages the outer side surface 90f of the lower bone 32f. To effect rotation of the wedge member 44f, a suitable tool is inserted into a socket 140f. Force is transmitted through the tool to the wedge member 44f urging the wedge member 44f to rotate in a clockwise direction from the position shown in FIG. 18 to the position shown in FIG. 19.

Upon initial application of the force to the wedge member 44f urging the wedge member to rotate in a clockwise direction (as viewed in FIG. 18), the pivot end portion 150f of the wedge member 44f is pressed against the outer side surface 90f of the lower bone 32f. At the same time, the side portion 134f of the wedge member 44f begins to slide along the outer side surface 88f on the upper bone 30f.

Continued application of force (torque) to the wedge member 44f results in the wedge member pivoting about an axis which extends through a location where the end portion 150f of the wedge member 44f engages the outer side surface 90f on the lower bone 32f. As the wedge member 44f pivots about the end portion 150f, the arcuate nose portion 128f moves into engagement with and slides along the outer side surface 88f on the upper bone 30f. As the wedge member 44f approaches the orientation shown in FIG. 19, the joint 34f is expanded and the spatial relationship between the upper and lower bones 30f and 32f is changed with a resulting change in the angular orientation of the upper and lower bones relative to each other.

When the wedge member 44f reaches the orientation shown in FIG. 19, the joint 34f has been expanded to the maximum extent possible by the wedge member. The wedge member 44f is then connected with the upper and lower bones 30f and 32f by suitable fasteners. The fasteners may extend through mounting tabs, similar to the mounting tabs 144 and 146 illustrated in FIG. 16 or the fasteners may extend through the wedge member in the manner illustrated schematically in FIG. 17. Of course, the wedge member 44f could be held in the upright (as viewed in FIG. 19) orientation in any one of many different manners by a suitable fastener arrangement.

Although only a single wedge member 44f has been shown in FIGS. 18-20, a plurality of the wedge members 44f could be used to expand the joint 34f and to transmit force between the bones 30f and 32f. Whether a single wedge member 44f or a plurality of wedge members 44f are used to expand the joint, the joint may be packed with bone growth promoting material.

Screw Type Wedge Member

In the embodiment of the invention illustrated in FIGS. 12-16, the wedge member 44d has a relatively smooth outer side surface 126. In the embodiment of the invention illustrated in FIGS. 21 and 22, the wedge member has a configuration similar to the configuration of a screw and has a irregular outer side surface. Since the embodiment of the invention illustrated in FIGS. 21 and 22 is generally similar to the embodiments of the invention illustrated in FIGS. 12-20, similar numerals will be utilized to designate similar components, the suffix letter "g" being associated with the numerals of FIGS. 21 and 22 to avoid confusion.

An upper bone 30g is connected with a lower bone 32g in a patient's body at a joint 34g. It should be understood that the joint 34g has been illustrated schematically in FIG. 21 and may be any joint in a patient's body. A rigid wedge member 44g is utilized to change the spatial relationship between the upper and lower bones 30g and 32g. The wedge member 44g is effective to expand at least a portion of the joint 34g when the wedge member 44g is inserted into the joint 34g.

The wedge member 44g has a thick end portion 50g and a thin end portion 52g. The wedge member 44g has an overall conical configuration. An external thread convolution 160 is formed on the wedge member 44g. The external thread convolution 160 has a spiral configuration and extends from the thick end portion 50g to the thin end portion 52g of the wedge member 44g.

Although the external thread convolution 160 could have many different configurations, the illustrated thread convolution has generally V-shaped crests and roots. The general configuration of the external thread convolution 160 is an American National Form Screw Thread and has a pitch cone with an angle of between five degrees and twenty degrees. Although one specific external thread convolution has been illustrated and described herein, it should be understood that the external thread convolution 160 could have a configuration of any one of many different known thread convolutions. It is believed that it may be desired to use known bone screw thread configurations for the configuration of the external thread convolution 160.

The rigid wedge member 44g may be formed of metal, ceramic, human or animal bone, or suitable polymeric materials. It is believed that it will be desirable to form the wedge member 44g of a material which is sufficiently rigid to withstand the forces transmitted between the upper and lower bones 30g and 32g. If desired, the wedge member 44g may be formed of a porous material having openings through which bone may grow. It is believed that it may be desired to coat the wedge member 44g with a bone growth promoting material.

When the wedge member 44g is to be utilized to change the spatial relationship between the upper and lower bones 30g and 32g, the thin end portion 52g of the wedge member 44g is pressed into the joint 34g between the upper and lower bones 30g and 32g. The wedge member 44g is then rotated about its longitudinal central axis 120g. A hexagonal recess 140g is provided in the wedge member 44g to facilitate the transmission of force from a suitable tool to the wedge member 44g.

As the wedge member 44g is rotated through a plurality of revolutions about its longitudinal central axis 120g, the external thread convolution 160g engages the upper and lower bones 30g and 32g. As the wedge member 44g is rotated about its longitudinal central 120g, the external thread convolution 160 engages the upper and lower bones 30g and 32g and pulls the wedge member into the joint 34g. As this occurs, the joint 34g is expanded and the spatial relationship between the upper and lower bones 30g and 32g is changed.

Once the wedge member 44g has moved into the joint 34g and the spatial relationship between the upper and lower bones 30g and 32g has been changed, the joint 34g may be packed with bone growth promoting materials and/or bone chips. It is contemplated that various known bone morphogenic proteins may be used with other osteoinductive materials to induce bone growth in the joint 34g. Although only a single wedge member 44g is illustrated in FIG. 21, a plurality of wedge members may be used if desired.

Bone Fitting Wedge Member

In the embodiments of the invention illustrated in FIGS. 1-11, the wedge members have flat upper and lower major side surfaces 54 and 56 (FIG. 6). In the embodiment of the invention illustrated in FIGS. 23 and 24, the wedge member has nonlinear side surfaces which have been shaped to correspond to the configuration of end portions of the bone at a joint between the bones. Since the embodiment of the invention illustrated in FIGS. 23 and 24 is generally similar to the embodiments of the invention illustrated in FIGS. 1-11, similar numerals will be utilized to designate similar components, the suffix letter "h" being associated with the numerals of FIG. 9 to avoid confusion.

Upper and lower bones 30h and 32h are interconnected at a joint 34h. The joint 34h is a schematic representation of any one of many joints in a patient's body. The joint 34h may be in a patient's wrist, ankle, hand, foot, back, or other portion of the patient's body.

When the spatial relationship between the upper and lower bones 30h and 32h is to be changed, a wedge member 44h is moved into the joint 34h. The wedge member 44h is moved into the joint with a thick end portion 50h of the wedge member trailing and a thin end portion 52h of the wedge member leading. As the wedge member 44h is pressed into the joint 34h, upper and lower major side surfaces 54h and 56h are pressed against outer side surfaces 88h and 90h on the upper and lower bones 30h and 32h. This results in expansion of the joint 34h in the manner previously described in conjunction with the embodiments of the invention illustrated in FIGS. 1-11.

In accordance with a feature of this embodiment of the invention, the upper and lower major side surfaces 54h and 56h on the wedge member 44h are configured to match the configuration of the outer side surfaces 88h and 90h on the upper and lower bones 30h and 32h, in the manner illustrated schematically in FIG. 24. By having the upper and lower major side surfaces 54h and 56h configured to match the configuration of the outer side surfaces 88h and 90h on the upper and lower bones 30h and 32h, the wedge member 44h is firmly seated against the bone and held against sidewise (as viewed in FIG. 24) movement relative to the bones. The arcuate configuration of the upper and lower major side surfaces 54h and 56h on the wedge member 44h extends from the thick end 50h of the wedge member 44h to the thin end 52h of the wedge member.

In the embodiment of the invention illustrated in FIG. 24, the wedge member 44h is formed of a rigid porous material having an open cell construction. A compartment or cavity 100h in the wedge member 44h holds bone growth inducing materials 110h. The bone growth inducing materials 110h may include bone morphogenic proteins and other osteoinductive materials. The joint 34h may be packed with bone growth promoting materials and/or bone chips.

The wedge member 44h is fixedly connected to the upper and lower bones 30h and 32h by suitable fasteners (not shown). The wedge member 44h may be connected with the upper and lower bones 30h and 32h by screws corresponding to the screws 70 and 72 of FIG. 8. Alternatively, the wedge member 44h may be connected with the upper and lower bone 30h and 32h by screws which extends through mounting tabs, corresponding to the mounting tabs 144 and 146 of FIG. 16. If desired, the wedge member 44h may be connected with only the upper bone 30h or only the lower bone 32h.

It is believed that by having the side surfaces 54h and 56h configured to correspond to the configuration of the surfaces 88h and 090h on the bones 30h and 32h, the joint 34h will be particularly stable when the joint has been immobilized by connecting the wedge member 44h to the bones. Although only a single wedge member 34h has been illustrated in FIGS. 22 and 24, a plurality of wedge members could be used to expand the joint. It is believed that the wedge member 44h may be particularly advantageous when vertebrae in a patient's back are to be interconnected.

Conclusion

In view of the foregoing description it is apparent that a new and improved method and apparatus is provided to change a spatial relationship between bones 30 and 32 which are interconnected at a joint 34 in a patient's body. When this is to be done, an opening is formed in a portion of the patient's body to expose the joint 34 interconnecting the bones 30 and 32. One of the bones 30 and 32 is moved relative to the other by expanding at least a portion of the joint 34 with a wedge member 44. The wedge member 44 is moved into the joint and applies force against the bones 30 and 32. The opening is closed with the wedge member 44 still disposed in the joint between the bones. Force is then transmitted between the bones 30 and 32 through the wedge member 44 to maintain the joint 34 in an expanded condition.

If the joint 34 is to be flexed after being expanded by the wedge member 44, the wedge member may be connected with only one of the bones 30 and 32. Alternatively, if the joint 34 is to be immobilized (fused) after inserting the wedge member 44, the wedge member may be fixedly connected with the bones 30 and 32 interconnected at the joint. The wedge member 44 may be porous and may be coated with and/or contain bone growth promoting material.

One embodiment of the wedge member 44 has major side surfaces 54 and 56 extending between thick and thin end portions 50 and 52 of the wedge member. The wedge member 44 is moved into the joint 34 with the thin edge portion 52 leading. As the wedge member 44 is moved into the joint 34, the thick trailing end portion 50 of the wedge member expands the joint.

In another embodiment of the invention, the wedge member 44d, 44e, 44f, or 44g may be rotated relative to the joint. In one embodiment of the invention, the wedge member 44g has a circular cross sectional configuration and has an external thread convolution 160 which extends from a thin leading end 52g of the wedge member to a thick trailing end 50g of the wedge member. The wedge member 44g is pressed into the joint 34g and rotated to cause the wedge member to expand the joint.

In another embodiment of the invention, the wedge member 44d, 44e or 44f has surface areas 134 and 136 which are relatively close together and other surface areas 128 and 130 which are relatively far apart. The wedge member 44d, 44e, or 44f is moved into the joint 34 with the surface areas 134 and 136 which are close together engaging the adjacent bones 30 and 32. The wedge member 44d, 44e or 44f is then rotated to apply force against the adjacent bones to expand the joint. The wedge member 44d or 44e may be rotated about its central axis 120 to apply forced against the bones 30 and 32 and expand the joint. Alternatively, the wedge member 44f may be rotated about a location where the wedge member engages one of the bones.

Regardless of which embodiment of the wedge members 44, 44a, 44b, 44c, 44d, 44e, 44f, 44g or 44h is selected, the wedge member may be used with any one of the many different bones and joints in a patient's body. The wedge member may be utilized at joints in a patient's wrist, ankle, hand, foot, back, or other portions of the patient's body. The use of the wedge member may be particularly advantageous when a joint between vertebrae in a patient's back is to be immobilized. One or more wedge members may be used to expand a joint to transmit force between bones.

What is claimed is:

1. An implantable device for maintaining an expanded condition of a vertebral joint between a first vertebra and a second vertebra, the implantable device comprising:
a body including a central longitudinal axis, a trailing end portion, a leading end portion, a first side portion, a second side portion, an upper surface and a lower surface, the upper surface defining a peripheral edge, a first passage extending through the trailing end portion and the upper surface and a second passage extending through the trailing end portion and the lower surface, a bone growth passage extending through the body between the upper surface and the lower surface, the bone growth passage surrounded by the peripheral edge, the bone growth passage includes an open upper end and an open lower end, wherein the open upper end is positioned at the upper surface, the bone growth passage configured to permit bone growth through the body, the central longitudinal axis positioned between the upper and lower surfaces of the body and being generally perpendicular to the bone growth passage, the first passage positioned on a first side of the central longitudinal axis and the second passage positioned on a second side of the central longitudinal axis, a leading thickness of the leading end portion being substantially consistent at a leading plane perpendicular to the central longitudinal axis, thereby defining a first leading thickness at the first side portion, a second leading thickness at the second side portion and a middle leading thickness between the first and second leading thicknesses, the first leading thickness, the second leading thickness and the middle leading thickness being substantially equal, a trailing thickness of the trailing end portion being substantially consistent at a trailing plane perpendicular to the central longitudinal axis, thereby defining a first trailing thickness at the first side portion, a second trailing thickness at the second side portion and a middle trailing thickness between the first and second trailing thicknesses, the first trailing thickness, the second trailing thickness and the middle trailing thickness being substantially equal, the trailing thickness being greater than the leading thickness.

2. The implantable device of claim 1, further comprising:
a first fastener having a first head and a first shaft, the first fastener positionable in the first passage; and
an second fastener having a second head and a second shaft, the second fastener positionable in the second passage, the first head positionable at least partially in the first passage in a mounted configuration and the second head positionable at least partially in the second passage in the mounted configuration.

3. The implantable device of claim 2, wherein the first head is positionable in a first countersink proximate a trailing end of the trailing end portion in the mounted configuration, the first shaft is positionable in a first channel in the mounted configuration, the second head is positionable in a second countersink proximate the trailing end in the mounted configuration and the second shaft is positionable in a second channel in the mounted configuration, the first passage comprised of the first countersink and the first channel, the second passage comprised of the second countersink and the second channel.

4. The implantable device of claim 3, wherein the first head is positionable entirely within the first countersink in the mounted configuration and the second head is positionable entirely within the second countersink in the mounted configuration.

5. The implantable device of claim 1, wherein the first passage includes a first countersink extending from a trailing end of the trailing end portion to a first channel, the first channel extending from the first countersink to the upper surface, the second passage includes a second countersink extending from the trailing end to a second channel, the second channel extending from the second countersink to the lower surface.

6. The implantable device of claim 1, wherein the body is constructed of a material selected from the group consisting of a human bone material, an animal bone material, a metallic material, a ceramic material and a polymeric material.

7. The implantable device of claim 1, wherein the body is constructed of a polymeric material.

8. The implantable device of claim 1, wherein the body includes a tooling socket aligned on the central longitudinal axis.

9. The implantable device of claim 1, wherein a leading end of the leading end portion is comprised of a blunt end portion.

10. The implantable device of claim 1, wherein the bone growth passage is packable with bone growth material.

11. The implantable device of claim 1, wherein the body includes first and second side surfaces, the first and second side surfaces being shaped to correspond to the configuration of end plates of the first and second vertebrae at the vertebral joint, respectively.

12. The implantable device of claim 1, wherein the body is coated with a material that promotes growth of bone.

13. The implantable device of claim 1, wherein the upper and lower surfaces taper toward each other from the trailing end portion to the leading end portion.

14. The implantable device of claim 1, wherein the upper and lower surfaces define an acute angle.

15. The implantable device of claim 14, wherein the acute angle is between one and thirty degrees (1-30°).

16. The implantable device of claim 14, wherein the acute angle is between five and twenty degrees (5-20°).

17. The implantable device of claim 1, wherein the upper surface defines an upper plane and the lower surface defines a lower plane, the first passage extending to the upper plane and the second passage extending to the lower plane.

18. The implantable device of claim 1, further comprising:
 a first countersink associated with the first passage at a trailing end of the trailing end portion; and
 a second countersink associated with the second passage at a trailing end of the trailing end portion.

19. The implantable device of claim 1, wherein the body is formed of a solid piece of material.

20. The implantable device of claim 1, wherein the body is formed by a piece of porous material.

21. The implantable device of claim 1, wherein the body is formed by a hollow piece of porous material.

22. An implantable device for maintaining an expanded condition of a vertebral joint between a first vertebra and a second vertebra, the implantable device comprising:
 a body including a trailing end portion, a leading end portion, a first side, a second side, an upper surface and a lower surface, a central longitudinal axis extending through the trailing end portion and the leading end portion, the body configured to slide into the vertebral joint in an insertion direction, the central longitudinal axis oriented generally parallel to the insertion direction, first and second passages formed in the body, the first passage extending through the trailing end portion at a first trailing end hole, the second passage extending through the trailing end portion at a second trailing end hole, the first trailing end hole and the second trailing end hole being positioned at opposite sides of the central longitudinal axis, a bone growth passage formed in the body having an open upper end at the upper surface and an open lower end at the lower surface, the bone growth passage being generally linear and extending generally perpendicular to the central longitudinal axis, the body having a peripheral edge defined at an intersection of the upper surface with the trailing end portion, the first side, the second side and the leading end portion, the peripheral edge surrounding the open upper end, the trailing end portion having a substantially constant trailing thickness taken at a trailing plane that is perpendicular to the central longitudinal axis, thereby defining a first trailing thickness at the first side, a second trailing thickness at the second side and a middle trailing thickness between the first and second trailing thicknesses, the first trailing thickness, the second trailing thickness and the middle trailing thickness being substantially equal, the leading end portion having a substantially constant leading thickness taken at a leading plane that is perpendicular to the central longitudinal axis, thereby defining a first leading thickness at the first side and a second leading thickness at the second side, the first leading thickness and the second leading thickness being substantially equal, the trailing thickness being greater than the leading thickness, the bone growth passage configured for packing with bone growth material to facilitate bone growth between the first vertebra and the second vertebra in a mounted configuration.

23. The implantable device of claim 22, further comprising:
 a first fastener having a first head and a first shaft, the first fastener positionable in the first passage with the first head proximate the first trailing end hole in the mounted configuration; and
 an second fastener having a second head and a second shaft, the second fastener positionable in the second passage with the second head proximate the second trailing end hole in the mounted configuration.

24. The implantable device of claim 23, wherein the first head includes a first rear surface and the first shaft includes first threads proximate a first front end, the second head includes a second rear surface and the second shaft includes second threads proximate a second front end, the first rear surface and the second rear surface positionable at a trailing end of the trailing end portion in the mounted configuration.

25. The implantable device of claim 23, wherein the first passage includes a first countersink in the trailing end portion and a first channel extending from the first countersink to the upper surface, the second passage includes a second countersink in the trailing end portion and a second channel extending from the second countersink to the lower surface.

26. The implantable device of claim 25, wherein the first shaft is positionable in the first channel and the second shaft is positionable in the second channel in the mounted configuration, first threads of the first fastener configured to engage hard cortical bone of the first vertebra in the mounted configuration, second threads of the second fastener configured to engage hard cortical bone of the second vertebra in the mounted configuration.

27. The implantable device of claim 22, wherein the bone growth material is constructed of a material selected from the group consisting of a bone morphogenic protein, an apatite composition with collagen, a demineralized bone powder and an osteoinductive material.

28. The implantable device of claim 22, wherein the body includes a socket in the trailing end portion aligned with the central longitudinal axis.

29. The implantable device of claim 28, wherein the socket is comprised of a tool socket.

30. The implantable device of claim 28, wherein the socket is comprised of a hexagonal recess.

31. The implantable device of claim 22, wherein a leading end of the leading end portion is comprised of a thin leading end.

32. The implantable device of claim 31, wherein the thin leading end comes to a sharp point.

33. The implantable device of claim 22, wherein a leading end of the leading end portion is comprised of a blunt end portion.

34. The implantable device of claim 22, wherein the body is formed of a rigid open cell material.

35. The implantable device of claim 22, wherein the first trailing end hole is horizontally aligned with the second trailing end hole.

36. The implantable device of claim 22, wherein the body is constructed of a polymeric material.

37. The implantable device of claim 22, wherein the first passage is positioned between the central longitudinal axis and the first side and the second passage is positioned between the central longitudinal axis and the second side.

38. The implantable device of claim 22, wherein the body is formed of a solid piece of material.

39. The implantable device of claim 22, wherein the body is formed by a piece of porous material.

40. The implantable device of claim 1, wherein the upper and lower surfaces are flat.

41. The implantable device of claim 1, wherein the body includes first and second side surfaces, the leading end portion includes a leading end, a first end defined at an intersection of the first side surface and the leading end and a second end defined at an intersection of the second side surface and the leading end, the leading end being substantially straight between the first end and the second end.

42. The implantable device of claim 41, wherein the first and second side surfaces are arcuate.

43. The implantable device of claim 1, wherein the leading end portion has a leading end and the trailing end portion has a trailing end, a body length defined between the trailing end and the leading end and the body having a width, the width being greater than the body length.

44. The implantable device of claim 22, wherein the upper and lower surfaces are flat.

45. The implantable device of claim 22, wherein the body includes first and second side surfaces, the leading end portion includes a leading end, a first end defined at an intersection of the first side surface and the leading end and a second end defined at an intersection of the second side surface and the leading end, the leading end being substantially straight between the first end and the second end.

46. The implantable device of claim 45, wherein the first and second side surfaces are arcuate.

47. The implantable device of claim 22, wherein the leading end portion has a leading end and the trailing end portion has a trailing end, a body length defined between the trailing end and the leading end and the body having a width, the width being greater than the body length.

* * * * *